US011893339B2

(12) United States Patent
Breber et al.

(10) Patent No.: US 11,893,339 B2
(45) Date of Patent: Feb. 6, 2024

(54) NATURAL-LANGUAGE MEDICAL RECORD GENERATION PLATFORM

(71) Applicant: Augmedix Operating Corporation, San Francisco, CA (US)

(72) Inventors: Sandra Breber, Orinda, CA (US); Sarah Niehaus, Ross, CA (US); Nathanael Wolfe, Oakland, CA (US); Patrick Cameron, Oakland, CA (US); Habibullah Al Hadi, Dacca (BD)

(73) Assignee: Augmedix Operating Corporation, San Francisco, CA (US)

( * ) Notice: Subject to any disclaimer, the term of this patent is extended or adjusted under 35 U.S.C. 154(b) by 0 days.

(21) Appl. No.: 17/313,482

(22) Filed: May 6, 2021

(65) Prior Publication Data
US 2021/0390265 A1 Dec. 16, 2021

Related U.S. Application Data
(60) Provisional application No. 63/038,498, filed on Jun. 12, 2020, provisional application No. 63/038,479, filed on Jun. 12, 2020.

(51) Int. Cl.
*G06F 40/166* (2020.01)
*G06F 3/0482* (2013.01)
(Continued)

(52) U.S. Cl.
CPC .......... *G06F 40/166* (2020.01); *G06F 3/0482* (2013.01); *G06F 3/0484* (2013.01);
(Continued)

(58) Field of Classification Search
CPC ...... G06F 40/166; G06F 40/40; G06F 3/0482; G06F 3/0484; G06F 2203/04803; G16H 10/60; G16H 20/10
See application file for complete search history.

(56) References Cited

U.S. PATENT DOCUMENTS 5,267,155 A 11/1993 Buchanan et al.
8,612,261 B1 12/2013 Swanson et al.
(Continued)

FOREIGN PATENT DOCUMENTS

CN 107633876 A 1/2018
CN 108447534 A 8/2018

OTHER PUBLICATIONS

Duke et al. (2014). "Regenstrief Institute's Medical Gopher: A next-generation homegrown electronic medical record system," International Journal of Medical Informatics (83): 170-179.
(Continued)

*Primary Examiner* — Nicholas Augustine
(74) *Attorney, Agent, or Firm* — MORRISON & FOERSTER LLP

(57) ABSTRACT

Systems and methods for generating a natural-language statement for a healthcare record are provided. A graphical user interface comprising a canvas region and a menu region is displayed, wherein menu region comprises a first set of one or more interactive graphical user interface menu objects configured to receive user inputs corresponding to medical information. Data is received representing a first user input comprising user interaction with one or more of the first set of menu objects, the first input indicating medical information for a patient. In accordance with the first user input, a natural-language statement is generated based on the medical information indicated by the first user input, and display of the canvas region is updated to display the natural-language statement.

31 Claims, 9 Drawing Sheets

(51) Int. Cl.
*G16H 10/60* (2018.01)
*G16H 20/10* (2018.01)
*G06F 40/40* (2020.01)
*G06F 3/0484* (2022.01)
*G06F 3/048* (2013.01)

(52) U.S. Cl.
CPC ............ *G06F 40/40* (2020.01); *G16H 10/60* (2018.01); *G16H 20/10* (2018.01); *G06F 2203/04803* (2013.01)

(56) References Cited

U.S. PATENT DOCUMENTS

| | | | |
|---|---|---|---|
| 10,541,053 B2 | 1/2020 | Sheffer et al. | |
| 10,949,602 B2* | 3/2021 | Snider | G10L 15/26 |
| 11,024,424 B2 | 6/2021 | Sun et al. | |
| 11,348,689 B1 | 5/2022 | Gonzales, Jr. | |
| 2003/0220819 A1 | 11/2003 | Burstein et al. | |
| 2011/0040576 A1 | 2/2011 | Madan et al. | |
| 2011/0078570 A1 | 3/2011 | Larsen et al. | |
| 2011/0238446 A1 | 9/2011 | Chaudhry | |
| 2012/0290310 A1 | 11/2012 | Watson | |
| 2013/0024382 A1* | 1/2013 | Dala | H04L 63/0464 705/51 |
| 2015/0178874 A1 | 6/2015 | Harris et al. | |
| 2016/0364532 A1 | 12/2016 | Honeycutt et al. | |
| 2017/0061093 A1 | 3/2017 | Amarasingham et al. | |
| 2017/0147751 A1 | 5/2017 | Schwartz et al. | |
| 2017/0213005 A1* | 7/2017 | Cox | G16H 40/67 |
| 2017/0220757 A1* | 8/2017 | Cox | G16H 40/63 |
| 2017/0220758 A1* | 8/2017 | Cox | G16H 10/60 |
| 2017/0235886 A1* | 8/2017 | Cox | G16H 10/60 705/3 |
| 2017/0235888 A1 | 8/2017 | Rahman et al. | |
| 2017/0235906 A1* | 8/2017 | Dorris | G16H 20/70 705/2 |
| 2017/0277854 A1* | 9/2017 | Kelly | G16Z 99/00 |
| 2017/0278209 A1* | 9/2017 | Olsen | G16H 10/60 |
| 2017/0364640 A1 | 12/2017 | Badawi | |
| 2018/0232489 A1 | 8/2018 | Fink et al. | |
| 2018/0373844 A1 | 12/2018 | Ferrandez-Escamez et al. | |
| 2019/0122750 A1 | 4/2019 | Ghosh et al. | |
| 2020/0237452 A1* | 7/2020 | Wolf | G06F 3/048 |
| 2021/0303630 A1 | 9/2021 | Atkinson | |
| 2021/0390249 A1 | 12/2021 | Breber et al. | |
| 2022/0084645 A1* | 3/2022 | Ginsburg | G16H 30/40 |
| 2022/0084664 A1* | 3/2022 | Ginsburg | G16H 15/00 |

OTHER PUBLICATIONS

Kaufman et al. (2016). "Natural Language Processing-Enabled and Conventional Data Capture Methods for Input to Electronic Health Records: A Comparative Usability Study," JMIR Med Inform 4(4): 1-20.

Lin et al. (2015). "Comparison of a semi-automatic annotation tool and a natural language processing application for the generation of clinical statement entries," American Medical Informatics Association 22: 132-142.

Minock et al. "Towards Building Robust Natural Language Interfaces to Databases," 13th International Conference on Applications of Natural Language to Information Systems, Jun. 24-27, 2008, London, UK; pp. 187-198.

Taira et al. (1999). "A Statistical Natural Language Processor for Medical Reports," AMIA Inc.: 970-974.

Wallace et al. (Jun. 2012). "Closing the Gap between Methodologists and End-Users: R as a Computational Back-End," Journal of Statistical Software 49(5): 1-15.

Breber et al., U.S. Office Action dated Dec. 15, 2022, directed to U.S. Appl. No. 17/315,540; 15 pages.

Breber et al., U.S. Office Action dated Jun. 23, 2023, directed to U.S. Appl. No. 17/313,540; 12 pages.

* cited by examiner

NATURAL-LANGUAGE MEDICAL RECORD GENERATION PLATFORM

CROSS-REFERENCE TO RELATED APPLICATIONS

This application claims benefit of priority of U.S. Provisional Patent Application No. 63/038,479, filed Jun. 12, 2020, and of U.S. Provisional Patent Application No. 63/038,498, filed Jun. 12, 2020, the entire contents of each of which are hereby incorporated by reference.

FIELD

This disclosure relates generally to electronic health record systems, and more specifically to user interfaces for automatically generating natural-language entries for electronic health records.

BACKGROUND

Creating electronic health records is a vital part of providing and documenting medical care across all medical fields and specialties. According to known techniques, medical practitioners manually write notes describing consultations with patients in order to record the patient's demographic information, prior medical information, previously-prescribed medication information, complaint and symptom information, and information regarding any treatment, tests, or medication prescribed for the patient during the consultation.

SUMMARY

As described above, notes regarding consultations with patients are created for electronic health records by being manually written by a medical practitioner. However, said known techniques are time-consuming and labor-intensive. Furthermore, manually creating notes for electronic medical records is prone to human error. Additionally, manually creating notes for electronic medical records may produce notes that are not in any standardized format and may therefore be poorly suited for future manual review/analysis and/or for future automated review/analysis.

Accordingly, there is a need for improved systems, methods, and/or user interfaces for creating electronic health records. Particularly, there is a need for improved systems, methods, and/or user interfaces for creating natural-language entries (e.g., notes) for storage in electronic health records in a manner that is fast, efficient, resistant to user error, flexible, configurable, and scalable. Furthermore, there is a need for said systems, methods, and/or user interfaces for creating natural-language entries (e.g., notes) for storage in electronic health records in a manner that encourages consistency of structure and content of the generated entries, such that the entries may be efficiently and accurately reviewed (whether manually or programmatically) after their creation and storage.

Disclosed herein are various systems, methods, computer-readable storage media, platforms, and graphical user interfaces that may address one or more of the above-identified needs. In some embodiments, the systems and methods disclosed herein may provide user interfaces for automatically generating natural-language entries for electronic health records. A computerized system may provide a front-end graphical user interface configured to be used by a medical professional or by a medical record management specialist to record patient medical information, such as information about a patient consultation. The interface includes a canvas portion and a menu portion, wherein the menu portion provides a plurality of graphical objects representing options that the user may select (or deselect) to indicate medical information about a patient. The indicated medical information may pertain to any aspect of patient medical information, such as a symptom, onset mode of a symptom, onset timing of a symptom, frequency (e.g., of a symptom), location of a symptom, contextual information, quality of a symptom, a prior medical condition, a current medication, a medication to be prescribed, a treatment to be prescribed, lab test results, a lab test to be ordered, imaging procedure results, an imaging procedure to be ordered, an organ system, a diagnostic procedure, and/or a diagnosis. Based on the options selected and/or information indicated by the user in one or more fields in the menu section, the system automatically generates a natural language sentence summarizing the information indicated by the user, and the natural language sentence is displayed in the canvas section of the graphical user interface. The menu options provided to the user and the structure of the automatically generated sentences/paragraphs may be based on a template selected by the user, wherein different available templates may be associated with different patient complains and/or different medical setting and use cases.

In some embodiment, a system for generating a natural-language statement for a healthcare record is provided, the system comprising one or more processors configured to cause the system to: display a graphical user interface comprising a canvas region and a menu region, wherein menu region comprises a first set of one or more interactive graphical user interface menu objects configured to receive user inputs corresponding to medical information; and receive data representing a first user input comprising user interaction with one or more of the first set of menu objects, the first input indicating medical information for a patient; in accordance with the first user input: generate a natural-language statement based on the medical information indicated by the first user input; and update display of the canvas region to display the natural-language statement.

In some embodiments, a non-transitory computer-readable storage medium storing instructions for generating a natural-language statement for a healthcare record is provided, the instructions configured to be executed by a system comprising one or more processors to cause the system to: display a graphical user interface comprising a canvas region and a menu region, wherein menu region comprises a first set of one or more interactive graphical user interface menu objects configured to receive user inputs corresponding to medical information; and receive data representing a first user input comprising user interaction with one or more of the first set of menu objects, the first input indicating medical information for a patient; in accordance with the first user input: generate a natural-language statement based on the medical information indicated by the first user input; and update display of the canvas region to display the natural-language statement.

In some embodiments, a method for generating a natural-language statement for a healthcare record, the method performed at a system comprising one or more processor, the method comprising: displaying a graphical user interface comprising a canvas region and a menu region, wherein menu region comprises a first set of one or more interactive graphical user interface menu objects configured to receive user inputs corresponding to medical information; and receiving data representing a first user input comprising user interaction with one or more of the first set of menu objects, the first input indicating medical information for a patient; in accordance with the first user input: generating a natural-language statement based on the medical information indicated by the first user input; and updating display of the canvas region to display the natural-language statement.

BRIEF DESCRIPTION OF THE FIGURES

Various embodiments are described with reference to the accompanying figures, in which:

FIGS. 2A-2D depict respective screens of a graphical user interface of a natural-language medical record generation platform, in accordance with some embodiments.

FIGS. 4A-4B depict respective screens of a graphical user interface of a natural-language medical record generation platform, in accordance with some embodiments.

DETAILED DESCRIPTION

Figure 1:
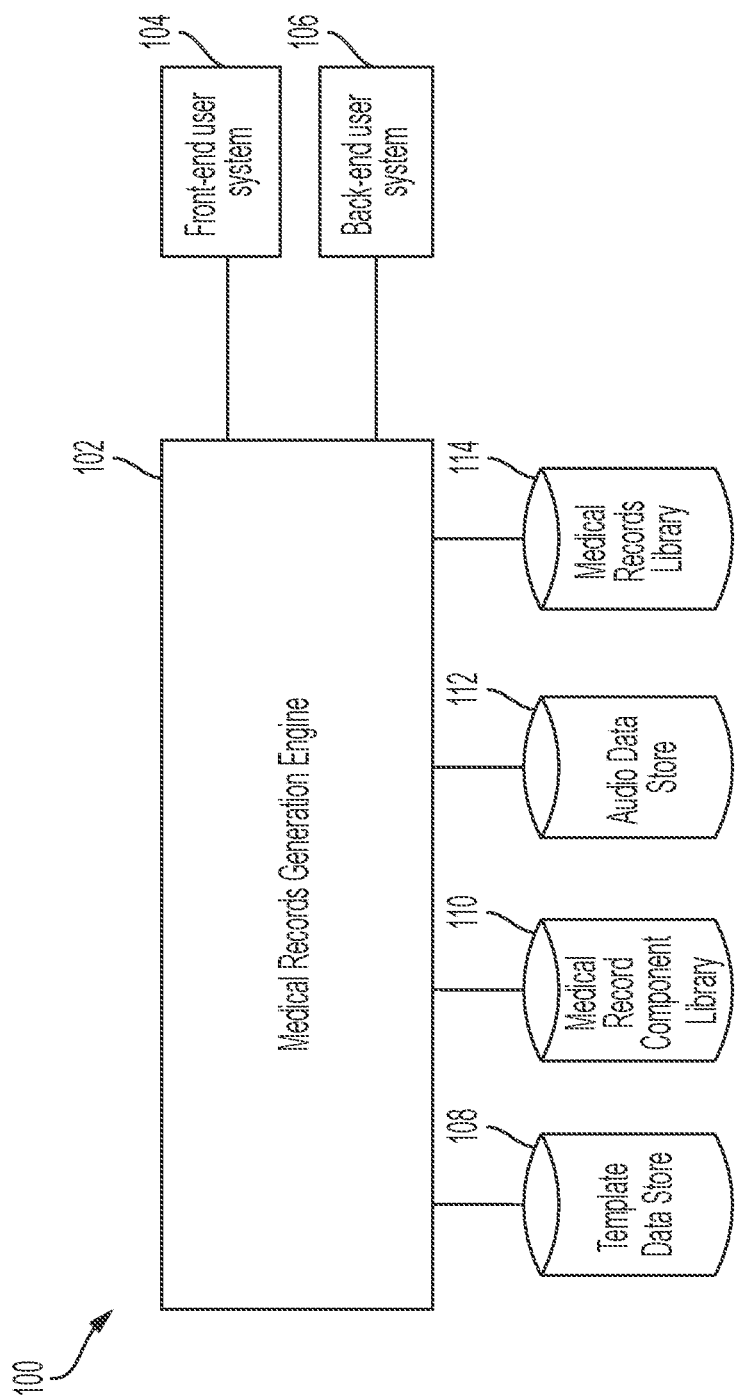
FIG. 1 depicts a system for providing a natural-language medical record generation platform, in accordance with some embodiments.

As described above and in further detail below, the disclosure herein pertains to various systems, methods, computer-readable storage media, platforms, and/or graphical user interfaces for automatically generating natural-language entries for electronic health records. A computerized system, for example as described below with reference to FIG. 1, may provide a front-end graphical user interface configured to be used by a medical professional or by a medical record management specialist to record patient medical information, such as information about a patient consultation. The system may, in some embodiments, be accessed by front-end users such as medical practitioners and/or medical records specialists (e.g., personnel tasked with creating and/or recording medical records). The system may be provided, in some embodiments, as locally-hosted software and/or by one or more servers providing the platform and graphical user interface via a network system (including by providing a GUI as part of a dedicated program/application and/or through a web-browser interface).

The graphical user interface provided to the front-end user, for example as described below with reference to FIGS. 3A-3D, may include a canvas portion and a menu portion, wherein the menu portion provides a plurality of graphical objects representing options that the user may select (or deselect) to indicate medical information about a patient. The indicated medical information may pertain to any aspect of patient medical information, such as a symptom, onset mode of a symptom, onset timing of a symptom, frequency (e.g., of a symptom), location of a symptom, contextual information, quality of a symptom, a prior medical condition, a current medication, a medication to be prescribed, a treatment to be prescribed, lab test results, a lab test to be ordered, imaging procedure results, an imaging procedure to be ordered, an organ system, a diagnostic procedure, and/or a diagnosis. Based on the options selected and/or information indicated by the user in one or more fields in the menu section, the system may automatically generate a natural language sentence summarizing the information indicated by the user, and the natural language sentence may be displayed in the canvas section of the graphical user interface.

The menu options provided to the user and the structure of the automatically generated sentences/paragraphs may be based on a template selected by the user, wherein different available templates may be associated with different patient complains and/or different medical setting and use cases. Various templates may define different options available for user selection via the GUI and may further define the natural-language sentence structure, paragraph structure, and/or document structure of the generated natural-language statements. Templates may be configured by back-end users (e.g., system administrators) and provided to front-end via locally-stored template data and/or template data provided via network communication (e.g., through a web-provided service).

FIG. 1 depicts a system 100 for providing a natural-language medical record generation platform, in accordance with some embodiments.

As shown in FIG. 1, system 100 may include medical records generation engine 102, front-end user system 104, backend user system 106, template data store 108, medical record component library 110, audio data store 112, and medical record library 114. As shown, each of the components of system 100 may be communicatively coupled (e.g., by wired and/or wireless electronic communication) with engine 102. In some embodiments, system 100 may be provided as a distributed (e.g., network) system with one or more components located remotely from one another and connected via network (e.g., wide-area network) communication. In some embodiment system 100 may be provided as a local system with one or more components located together with one another and connected via local network communication. In some embodiments, one or more components of system 100 may be provided as part of a single computer device. As explained herein, system 100 may provide a platform by which a front-end user of system 104 may be provided with one or more GUI's as described herein to generate and store natural-language entries for electronic health records.

Medical records generation engine 102 may comprise any one or more processors (located locally and/or remotely from front-end system 104 and/or back-end system 106) configured to perform all or part of any of the techniques disclosed herein. In some embodiments, engine 102 may be provided, in whole or in part, as one or more processors of a personal computer, laptop computer, tablet, mobile electronic device, server, distributed computing system, and/or cloud computing system.

Engine 102 may be configured to provide one or more graphical user interfaces (e.g., the interface described below with respect to FIGS. 3A-3D) to front-end users of the system such that the front-end users may supply information to system 100 regarding a patient medical consultation. For example, engine 102 may provide instructions for providing one or more graphical user interface screens to system 104 such that system 104 may display a graphical user interface and receive user inputs via said graphical user interface.

Engine 102 may then receive (via wired or wireless electronic transmission) data transmitted from front-end user system 104 regarding the user inputs detected by system 104. Based on the data received regarding front-end user input, engine 102 may generate a natural-language statement for entry into an electronic health record, wherein the natural language statement may describe one or more aspects of the patient consultation corresponding to the executed front-end user inputs. For example, the natural language statement may describe patient demographic information, patient background information, patient medical/family history information, patient complaint information, patient symptom information, patient preexisting/past medication information, patient preexisting/past treatment information, medication prescription information, test/analysis prescription information, and/or treatment prescription information. A natural-language phrase, sentence, or paragraph may be automatically generated based on a natural-language phrase structure, sentence structure, and/or paragraph structure accessible to engine 102 (e.g., stored as part of a template data structure on template data store 108). Once the natural-language statement is generated, the statement may be stored (e.g., as part of an electronic health record in medical records library 114) and/or displayed to a user (e.g., by being transmitted to front-end user system 104 for display on a display).

Front-end user system 104 may comprise any one or more computer systems (located locally and/or remotely from engine 102) configured to receive instructions and/or transmitted data from engine 102, to render and/or display a graphical user interface to a front-end user, to detect one or more inputs executed against the graphical user interface by the user, and to transmit data regarding detected user inputs to engine 102. In some embodiments, front-end user system 104 may include any suitable display and any suitable input device (e.g., mouse, keyboard, touch-sensitive device, touch-screen, microphone, etc.). In some embodiments, front-end user system 104 may be provided, in whole or in part, as a personal computer, workstation computer, laptop computer, tablet, or mobile electronic device.

Back-end user system 106 may comprise any one or more computer systems (located locally and/or remotely from engine 102) configured to send data to and/or receive data from engine 102. In some embodiments, back-end system 106 may be configured to send instructions to engine 102 in order to configure the user interface to be provided to front-end system 104, such as by configuring options to be presented to front-end users of the interface and/or configuring natural-language sentence structures and/or paragraph structures to be used to create medical notes. In some embodiments, back-end system 106 may be configured to receive transmissions from engine 102 regarding monitoring front-end users, system performance, system characteristics, and/or metadata collected based on use of the platform and graphical user interfaces by one or more front-end users. In some embodiments, back-end user system 106 may include any suitable display and any suitable input device (e.g., mouse, keyboard, touch-sensitive device, touch-screen, microphone, etc.). In some embodiments, back-end user system 106 may be provided, in whole or in part, as a personal computer, workstation computer, laptop computer, tablet, or mobile electronic device.

In some embodiments, template data store 108 may comprise any one or more computer-readable storage mediums configured to store template data. Template data may include data (e.g., one or more data structures) configured to be usable by engine 102 to provide all or part of the contents of a GUI to a user of front-end user device 104. In some embodiments, templates may govern what options are displayed to a front-end user of the system and the manner in which they are displayed to the user, as well as governing the manner in which the system generates natural-language statements based on user inputs. In some embodiments, template data store 108 may store different templates for different use cases, including different medical specialties, different languages, different countries, different regions, different states, different medical facilities, different doctors, different patient characteristics or classes, and/or different complaint types. In some embodiments, a front-end user may select an appropriate template based on the nature of the patient consultation (e.g., based on the purpose of the patient visit and/or what the patient's complaint is), and the selected template may cause the system to display appropriate and relevant options for such a consultation.

In some embodiments, templates stored in template data store 108 may be created, updated/modified, and/or deleted by system 100. In some embodiments, a back-end user of system 106 may create, modify, or delete a template by executing inputs comprising instructions to do so to system 108. In some embodiments, system 108 and/or system 100 may automatically update a template based on metadata collected regarding use of the template by one or more front-end users (e.g., if an option in the template is rarely selected, the option may be deprioritized in the template such that it is presented in a less prominent manner (e.g., further down in a list); or, if an option that is not automatically presented in a template is frequently manually added by users of the template, then the option may be added to the template such that it is automatically presented in the future).

In some embodiments, medical record component library 110 may comprise any one or more computer-readable storage mediums configured to store component information that may be used in the creation of electronic health records and/or in the creation of templates for use in the systems described herein. For example, medical record component library 110 may store data pertaining to medical specialty information, patient visit type information, patient complaint type information, complaint-element information, descriptor information (e.g., information regarding options that may be selected by users to characterize one or more complaint-elements), treatment information, test information, diagnosis information (e.g., diagnosis code information), imaging information, medications information, and/or health systems information.

The data stored in library 110 may in some embodiments be used to create (e.g., incorporated into) and/or referenced by (e.g., the system may execute a call to read the data in library 110) a template executed by the system to provide a graphical user interface for a front-end user. For example, a template may be configured to provide a plurality of options to a front-user for specifying what treatments are being prescribed to a patient; the options for the template may be populated by being automatically drawn from one or more lists or sets of treatment information stored in library 110. In some embodiments, a template may populate a set of options based on an entire dataset or an entire data subset from library 110; in some embodiments, a template may populate a set of options based on a selection of specific data items from library 110, such as items specified by a back-end user of system 108 in creating the template.

In some embodiments, audio data store 112 may comprise any one or more computer-readable storage mediums configured to store audio data. In some embodiments, audio data may be used to provide one or more user inputs, for example by using NLP to translate for conversation to inputs, and/or to copy/paste dictations using one or more speech-to-text tools. In some embodiments, inputs for the system may be user-generated and/or may be audio-generated using one or more NLP models.

In some embodiments, medical record library 114 may comprise any one or more computer-readable storage mediums configured to store medical records data such as electronic health records. In some embodiments, medical records data stored on library 114 may include natural-language medical record entry data (e.g., notes) generated by engine 102 in accordance with one or more of the technique described herein.

FIGS. 2A-2D depict respective screens 200a-200d of graphical user interface 200 of a natural-language medical record generation platform, in accordance with some embodiments. In some embodiments, GUI 200 may be displayed by a display of front-end user system 104 of system 100, such that a user of GUI 200 may execute inputs via GUI 200 in order to cause system 100 generate a natural-language entry (e.g., a note) pertaining to a patient consultation for storage as part of an electronic health record. For the purposes of the description of FIGS. 2A-2D herein, a front-end user entering information into interface 200 regarding a patient consultation may be referred to either as a user or as a "scribe." Various functionalities of the systems and platforms disclosed herein are described below with reference to GUI screens 200a-200d.

Figure 2A:
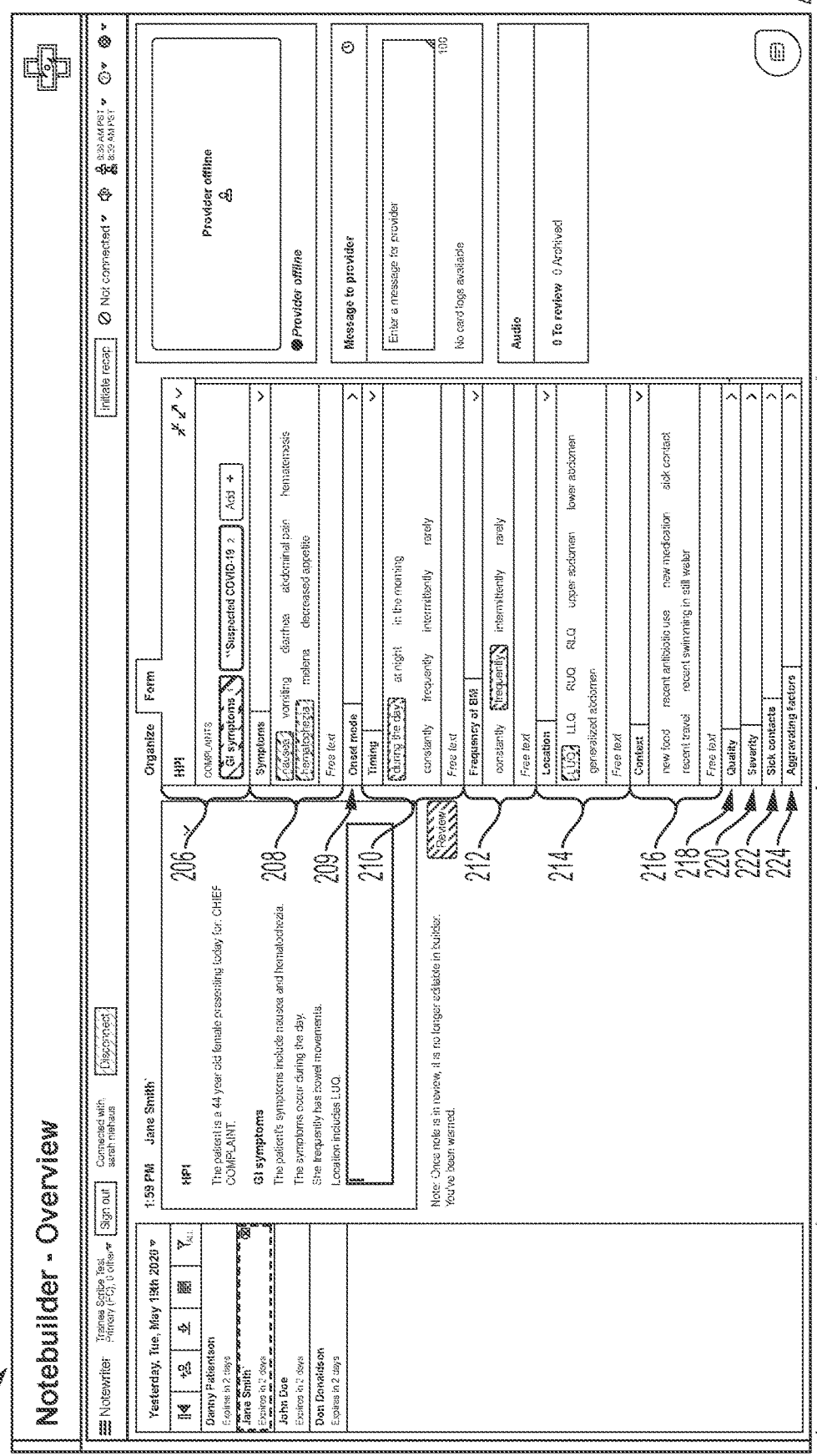

FIG. 2A depicts screen 200a of graphical user interface 200, in accordance with some embodiments. Screen 200a depicts GUI 200 during the process of capturing patient information during a patient consultation, and the description of screen 200a below provides an overview of certain functionalities of the systems and platforms disclosed herein. As shown in FIG. 2A, screen 200a comprises canvas region 202a and menu region 204a.

In some embodiments, canvas region 202a is a region of GUI 200 on which natural-language phrases, sentences, and/or paragraphs are generated based on user inputs that are executed via GUI 200. As shown in the example of FIG. 2A, canvas region 202a displays a natural-language sentence describing patient demographic information and including a placeholder for the patient's chief complaint (the placeholder may be replaced by a statement of the patient's chief complaint once an option indicating the chief complaint is selected or otherwise indicated by a user/scribe). As shown further in region 202a, region 202a displays four natural-language statements regarding the patient's complaint for GI symptoms. The natural-language statements regarding demographic information and those regarding complaint information may be generated and dynamically updated for display in canvas region 202a in real-time based on options selected and/or information inputted by the user to menu region 204a, described below in additional detail. By updating canvas region 202a in real-time, a user may receive immediate feedback regarding how selection of one or more options will affect the creation of a natural-language statement for entry into a medical record.

In some embodiments, menu region 204a is a region of GUI 200 on which a menu of various GUI objects representing various options are displayed to the user. The GUI objects displayed in menu region 202a may include one or more of the following: selectable and/or buttons/icons, drop-down menus and/or scrollable menus, character entry fields, and/or number entry fields. As shown by the examples in region 204a in screen 200a, the various GUI objects in region 202a may be configured to allow a user of GUI 200 to indicate various information about the patient consultation, including by typing in information into a field, selecting an option from a menu, and/or selecting or deselecting a button/icon option.

As shown by the examples in menu region 204a in screen 200a, GUI objects in menu region 204a may be used to indicate various aspect of information regarding a patient's complaint. In some embodiments, GUI objects may be arranged within menu region 204a into a plurality of sub-regions within menu region 204a. The option sub-regions within menu region 204a may include logically related options that may be used by a user to describe a certain aspect of a patient's symptoms, complaint information, demographic information, or other information.

In the example of FIG. 2A, menu region 204a includes complaints sub-region 206a, symptoms sub-region 208a, onset mode sub-region 209a, timing sub-region 210a, frequency sub-region 212a, location sub-region 214a, context sub-region 216a, quality sub-region 218a, severity sub-region 220a, sick contacts sub-region 222a, and aggravating factors sub-region 224a. (Other sub-regions may be included depending on the template being applied and/or in accordance with the patient, symptom, complaint, medical history, etc.) As shown, sub-regions may be displayed in a collapsed or expanded state, and a user may click or tap on a sub-region in order to toggle it between the expanded and collapsed states. In the example shown, sub-regions 206a, 208a, and 210a-216a are in an expanded state while sub-regions 209a and 218a-224a are in a collapsed state.

In some embodiments, complaints sub-region 206a may be configured to allow a user to indicate information regarding one or more complaints for a patient and/or to display one or more previously-indicated complaints. In some embodiments, a complaints sub-region may include a text entry field into which a user may type in order to search for and select one or more predefined complaint options. In the example shown in sub-region 206a, two icons show that the user has indicated a patient complaint of GI symptoms and a patient complaint of suspected COVID-19.

As further shown in sub-region 206a, a selectable "Add" icon may be selected (e.g., clicked or tapped) by a user in order to display a field allowing the user to search for and/or add one or more additional complaints. In some embodiments, one or more complaints displayed in a complaints sub-region may be pre-populated based on information entered by a user at a different screen of GUI 200 (e.g., at a setup screen or an organization screen as described below with reference to FIG. 2B).

In some embodiments, a user may be able to select (e.g., tap or click) one of the GUI objects (e.g., icons) representing a complaint in order to cause GUI 200 to display one or more other sub-regions and/or GUI objects associated with the selected complaint. In the example shown in FIG. 2A, the user has selected the icon representing the "GI symptoms" complaint in sub-region 206a, and region 204a of screen 200a is accordingly displaying sub-regions 208a-224a which pertain to the GI symptoms complaint.

In some embodiments, symptoms sub-region 208a may be configured to allow a user to indicate information regarding one or more symptoms for a patient. In some embodiments, the symptoms indicated may be associated by the system with a respective complaint under which the user is working.

As shown in FIG. 2A, symptoms sub-region 208a comprises a plurality of icons/buttons that may be selected and/or deselected by a user of GUI 200, for example by tapping or clicking the icons/buttons. In some embodiments, a user may tap or click the icon/button in order to toggle it between not selected and selected; between not selected and deselected; between selected and deselected; or between not selected, selected, and deselected. In some embodiments, not selecting an option may indicate an absence of information associated with the option (e.g., the symptom is not reported as being present nor as being absent), selecting an option may affirm the information associated with the option (e.g., the symptom is reported as present), and deselecting an option may expressly disaffirm the information associated with the option (e.g., the symptom is expressly reported as being not present). In some embodiments, a button/icon may toggle between different appearances, shadings, and/or colors to indicate whether the button/icon is not selected (e.g., gray), selected (e.g., green), or deselected (e.g., red).

In some embodiments, GUI 200 may be configured to require a user to make a selection or deselection of any one or more options within an option group (e.g., a group of options displayed in a sub-region, or a subgroup of options displayed within a sub-region). In some embodiments, GUI 200 may be configured to require a user to make a selection or deselection of a specific option (e.g., the user may be disallowed from leaving the option neither selected nor deselected). In some embodiments, a user may be able to leave one or more (or all) options in a group neither selected nor deselected. (In some embodiments, a sub-region may include a single option group; in some embodiments, sub-region may include multiple separate option groups.)

In some embodiments, a user may not be permitted to select more than predetermined maximum number of options in an option group, wherein the predetermined maximum number of options may be as low as 1 (or in some embodiments may be as low as 0, e.g., if one or more other selections made by the user in a different sub-region of GUI 200 logically preclude selection of any of the options in the group). In some embodiments, a user may permitted to select any number of options in an option group. In some embodiments, a user may be required to select a number of options in an option group within a predetermined range. In some embodiments, a user may be required to select exactly a predetermined number of options in an option group.

In the example of sub-region 208a in FIG. 2A, sub-region 208a includes eight option buttons each representing a potential symptom. As shown, the user has selected two of the options—"nausea" and "hematochezia"—and left the other six options not selected. Accordingly, the system has generated a natural-language statement regarding the two selected symptom options and displayed said statement in the canvas region of screen 200a: "The patient's symptoms include nausea and hematochezia."

In addition to the selectable option buttons/icons, sub-region 208a also includes a free text field into which a user may manually type a statement or other text. In some embodiments, text typed into the free text field may be inserted directly into the natural-language entry being generated and displayed on canvas portion 202a. In some embodiments, text typed into the free text field of a sub-region may be displayed immediately after (or immediately before) any automatically-generated text created on the basis of the options that are (or are not) selected or deselected in the option group. Thus, in the example of sub-region 208a, text entered into the free text field may be displayed in canvas region 202a after the sentence "The patient's symptoms include nausea and hematochezia." The grammatical structure of the natural language statement(s) generated and displayed in canvas portion 202a, including the manner in which said statement(s) incorporate(s) one or more options that are selected or deselected in menu region 204a, may be determined by the system (e.g., engine 102) in accordance with a template being applied to the patient consultation.

The other sub-regions 209a-224a shown in FIG. 2 may include similar sets of selectable and/or deselectable options, may include similar free-text fields, and may be configured to allow a user to generate a natural-language statement based on selection and/or deselection of options in a similar manner as described above with reference to sub-region 206a.

In some embodiments, onset sub-region 209a may be configured to allow a user to indicate information regarding symptom onset for a patient. In some embodiments, the symptom onset information may be associated by the system with a respective complaint under which the user is working.

In some embodiments, timing sub-region 210a may be configured to allow a user to indicate information regarding symptom timing for a patient. In some embodiments, the symptom timing information may be associated by the system with a respective complaint under which the user is working. As shown, timing sub-region 210a includes a free-text field as well as seven option buttons each representing a potential symptom timing descriptor. As shown, the user has selected one of the options—"during the day"—and left the other six options not selected. Accordingly, the system has generated a natural-language statement regarding the selected symptom timing option and displayed said statement in the canvas region of screen 200a: "The symptoms occur during the day."

In some embodiments, frequency sub-region 212a may be configured to allow a user to indicate information regarding symptom frequency or the frequency of any other medically-relevant occurrence (e.g., frequency of bowel movements) for a patient. In some embodiments, the frequency information may be associated by the system with a respective complaint under which the user is working. As shown, frequency sub-region 212a includes a free-text field as well as four option buttons each representing a potential frequency descriptor. As shown, the user has selected one of the options—"frequently"—and left the other three options not selected. Accordingly, the system has generated a natural-language statement regarding the selected frequency option and displayed said statement in the canvas region of screen 200a: "She has bowel movements frequently."

In some embodiments, location sub-region 214a may be configured to allow a user to indicate information regarding symptom location for a patient. In some embodiments, the symptom location information may be associated by the system with a respective complaint under which the user is working. As shown, location sub-region 214a includes a free-text field as well as seven option buttons each representing a potential frequency descriptor. As shown, the user has selected one of the options—"LUQ"—and left the other six options not selected. Accordingly, the system has generated a natural-language statement regarding the selected location option and displayed said statement in the canvas region of screen 200a: "Location includes LUQ."

In some embodiments, context sub-region 216a may be configured to allow a user to indicate information regarding contextual information for a patient. In some embodiments, the contextual information may be associated by the system with a respective complaint under which the user is working. As shown, context sub-region 216a includes a free-text field as well as six option buttons each representing a potential frequency descriptor. As shown, the user has not selected any of the option buttons in context sub-region 216a, and there is accordingly no natural-language statement regarding context options generated and displayed in the canvas region of screen 200a.

In some embodiments, quality sub-region 218a may be configured to allow a user to indicate information regarding symptom quality for a patient. For example, a symptom quality may be a descriptor that characterizes a quality of a symptom, such as "stabbing" pain, "dull" pain, or "throbbing" pain. In some embodiments, the symptom quality information may be associated by the system with a respective complaint under which the user is working.

In some embodiments, severity sub-region 220*a* may be configured to allow a user to indicate information regarding symptom severity for a patient. For example, a symptom severity may be a descriptor that characterizes a severity of a symptom, such as "intense" pain, "moderate" pain, or "mild" pain. In some embodiments, the symptom severity information may be associated by the system with a respective complaint under which the user is working.

In some embodiments, sick contacts sub-region 222*a* may be configured to allow a user to indicate information regarding contacts for a patient. In some embodiments, a contact may indicate a person, place, or activity with which the patient has been in contact. In some embodiments, the contacts information may be associated by the system with a respective complaint under which the user is working.

In some embodiments, aggravating factors sub-region 224*a* may be configured to allow a user to indicate information regarding aggravating factors for a patient. In some embodiments, the aggravating factor information may be associated by the system with a respective complaint under which the user is working.

As shown by the natural-language statements displayed in canvas region 202*a*, the system (e.g., system 100) has generated various natural-language statements in accordance with options selected (e.g., buttons selected) by the user in menu region 204*a* of GUI 200. In some embodiments, one statement may be generated and displayed per option selected. In some embodiments, multiple selected options may be included in a single statement (e.g., by being listed in series with one another). In some embodiments, one or more option from different option groups—e.g., from different sub-regions of menu region 204*a* and pertaining to different types of information—may be included in a single natural-language sentence together with one another; for example, a generated sentence may describe both a symptom identity and its timing (e.g., "The patient reports frequent nausea.").

In some embodiments, canvas region 202*a* may display different natural-language statements separately from one another (e.g., by displaying them on different lines from one another). For example, a natural language-statement generated in accordance with inputs executed via a first sub-region of menu region 204*a* may be displayed on a separate line from a natural-language statement executed via a second sub-region of menu region 204*a*. In this way, a user of GUI 200 may be able to easily view changes as they are dynamically made to different natural-language statements in canvas region 202*a* as the user selects and/or deselects different options in menu region 204*a*.

In some embodiments, canvas region 202*a* may display one or more of the generated natural-language statements in a predefined paragraph structure, section structure, and/or document structure. For example, as shown in FIG. 2A, the sentences generated and displayed in region 202*a* are displayed under two separate headings (the headings shown in bold) with one sentence under the first heading and four sentences under the second heading. The arrangement of one or more sentences into different paragraphs, sections, headings, etc. in canvas region 202*a* may be defined by system 200 in accordance with a template being applied to generation of the natural-language entry for storage in an electronic health record.

In some embodiments, the arrangement of one or more generated statements into different paragraphs, sections, headings, etc. in canvas region 202*a* may be the same or different from the arrangement of the same generated statements in a review format and/or output format generated by the system and used for storage of the natural-language statements in an electronic health record. For example, canvas region 202*a* may display one or more statements on individual lines for easy viewing and editing during a note creation process, whereas the system may then collapse one or more of those sentences into a single line or into a single paragraph upon approval of the sentences by the user, such that the sentences are saved in a unified paragraph form in the electronic health record.

In addition to canvas region 202*a* and menu region 204*a*, screen 200*a* of GUI 200 further includes patient visit selection region 226*a*. In some embodiments, region 226*a* may be configured to allow a user of GUI 200 to select a patient visit under which a natural-language entry for a medical record (e.g., a note) should be created. In some embodiments, a user may first specify a patient visit and then specify information about patient demographics, patient complaint, and all other medical information in menu region 204*a* afterwards, such that all specified information may be associated with the indicated patient visit. In some embodiments, there may be a one-to-one relationship between a patient visit and a note (or other natural-language entry for storage in a medical record) generated by the system, such that the system may be configured to create and store one note per patient visit.

In some embodiments, region 226*a* may be configured to display patients and/or patient visits in list form, such that a user may click or tap to select a patient and/or patient visit. In some embodiments, options for selecting a patient visit may be nested under options for selecting a patient, such that different visit options may be displayed as items under a patient dropdown option. In some embodiments, one or more GUI objects (e.g., selectable icons) may be displayed for allowing a user to add a new patient and/or a new visit.

Selecting a patient visit and/or adding a new patient visit may, in some embodiments, automatically cause display of a canvas region and menu region for building a note for the selected and/or newly-added visit.

In some embodiments, selecting and/or adding a new patient visit may cause the system to automatically import patient demographic information (e.g., into a menu region, as discussed below with respect to FIG. 2B) based on demographic information entered for the patient during creation of another note pertaining to another visit.

Figure 2B:
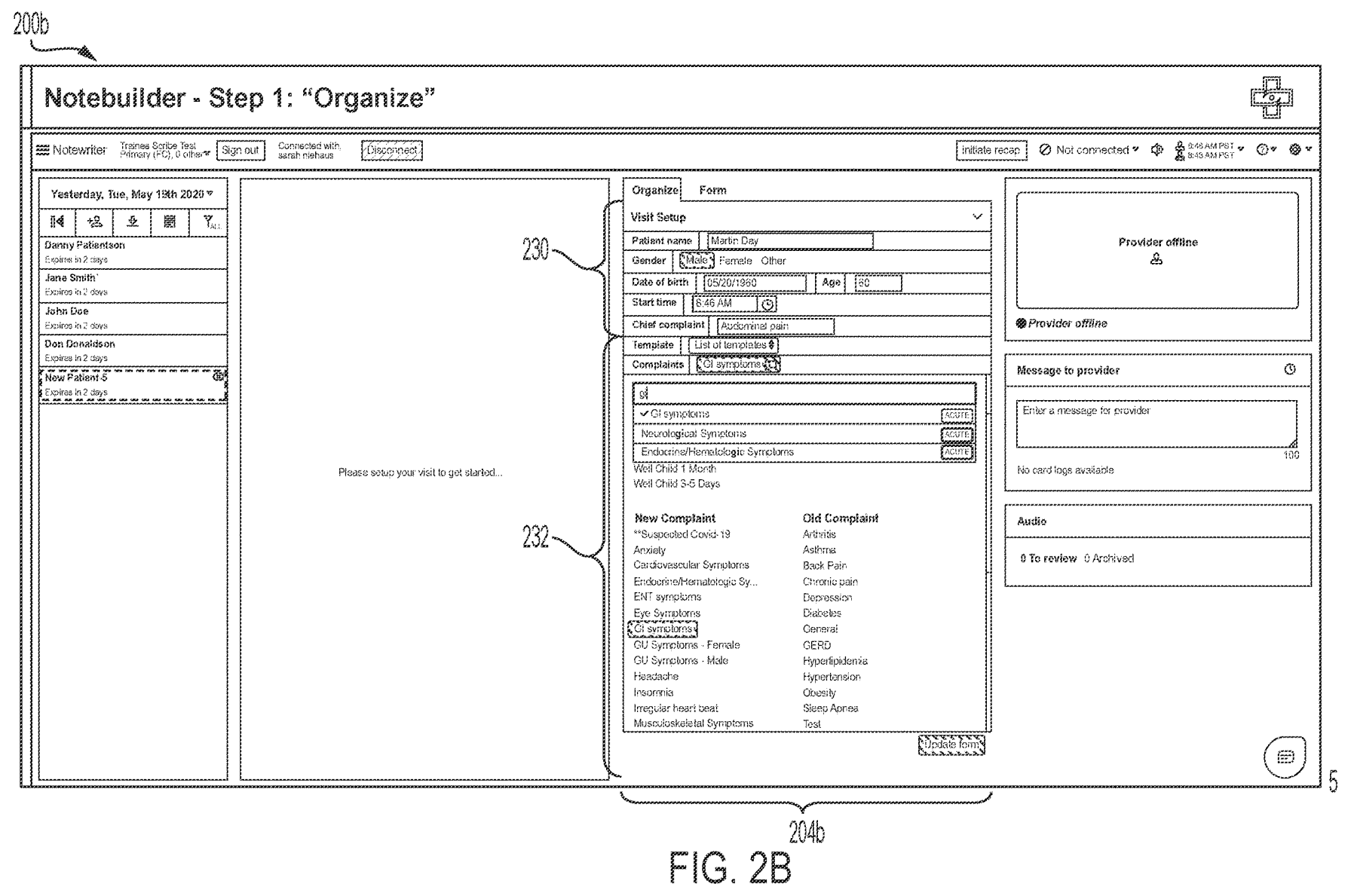

FIG. 2B depicts screen 200*b* of a graphical user interface 200, in accordance with some embodiments. Screen 200*b* depicts GUI 200 during the process of organizing or setting up the interface for capture of information during a patient visit. As shown in FIG. 2B, no canvas region is displayed during the setup process, and instead the user is prompted to specify patient demographic information and patient complaint information in menu region 204*b* before the canvas region is displayed. The description of screen 200*b* below provides an overview of certain functionalities of the systems and platforms disclosed herein, with aspects of screen 200*b* that are the same or similar as screen 200*a* not described or described only briefly, and with corresponding reference numerals used for same/similar portions of the screens (e.g., menu region 204*b* may share one or more features in common with menu region 204*a*).

As shown in FIG. 2B, menu region 204*b* of screen 200*b* displays options for an "organize" step of the note-building process, as opposed to the options for the "capture" step of the note-building process described above with reference to screen 200*a* in FIG. 2A. In some embodiments, an "organize" step may refer to the step of capturing patient demographic information, patient consultation metadata, and/or the identity of one or more patient complaints to be used to determine which template should be selected by the system and used to provide GUI screens for capturing patient medical information regarding the patient's symptoms and other medical information relevant to the specified complaints. In some embodiments, a user of GUI 200 may select one or more complaints at the "organize" step before the system provides one or more GUI screens for inputting symptom information and other information relevant to the complaint during the patient consultation.

As shown in FIG. 2B, menu region 204b may include demographic information region 230 and complaint selection region 232.

Demographic region 204b may be a GUI region configured to accept inputs from a user regarding patient demographic information including but not limited to name, gender, and date of birth. Demographic region 204b may be further configured to accept inputs from a user regarding consultation metadata, such as consultation time and/or location. In some embodiments, demographic information indicated via a demographic region of a GUI may be used by the system to filter available complaints, to configure a template for collecting symptom information and/or medical information at a capture stage, and/or to configure natural-language phrases generated by the system using appropriate pronouns.

Complaint selection region 232 may be a GUI region configured to accept inputs from a user regarding one or more complaints to be associated with the patient consultation. In some embodiments, complaint selection region 232 may include a text field into which a user may type a chief complaint. In some embodiments, complaint selection region 232 may include a search field into which a user may type text to search for one or more complaints to be added to associated with the consultation; in some embodiments, the complaint template used by the system to generate and/or provide the user interface screens for capturing patient symptom and medical information may be generated, selected, and/or configured in accordance with the one or more complaints indicated by the user via complaint selection region 232.

In some embodiments, a complaints selection region may be configured to allow a user to specify one or more complaints via typing into a text field, selecting from a drop down menu, and/or selecting from a list of displayed options. In some embodiments, as a user types into a search field, suggested complaints to be added to the template may be automatically displayed to the user. In some embodiments, suggested complaints may be organized into a group of "new complaints" and a group of "old complaints" according to records accessible by the system regarding what complaints the same patient has previously presented with. In some embodiments, the displayed suggested complaints may be selectable user interface icons that can be clicked or tapped by a user in order to be added to the template being configured for the patient consultation. In some embodiments, the suggested complaints that are displayed to the user may be filtered, automatically and/or in accordance with user input, in accordance with clinician specialty, medical facility, country region, state, patient identity, patient demographic information, and/or reason for patient visit.

As shown in the example of FIG. 2B, the user has clicked on "GI Symptoms" under the heading "New Complaint", and a "GI Symptoms" complaint has been added to the template being configured, such that prompts for information regarding GI Symptoms will subsequently be displayed to the user at the capture stage.

Figure 2C:
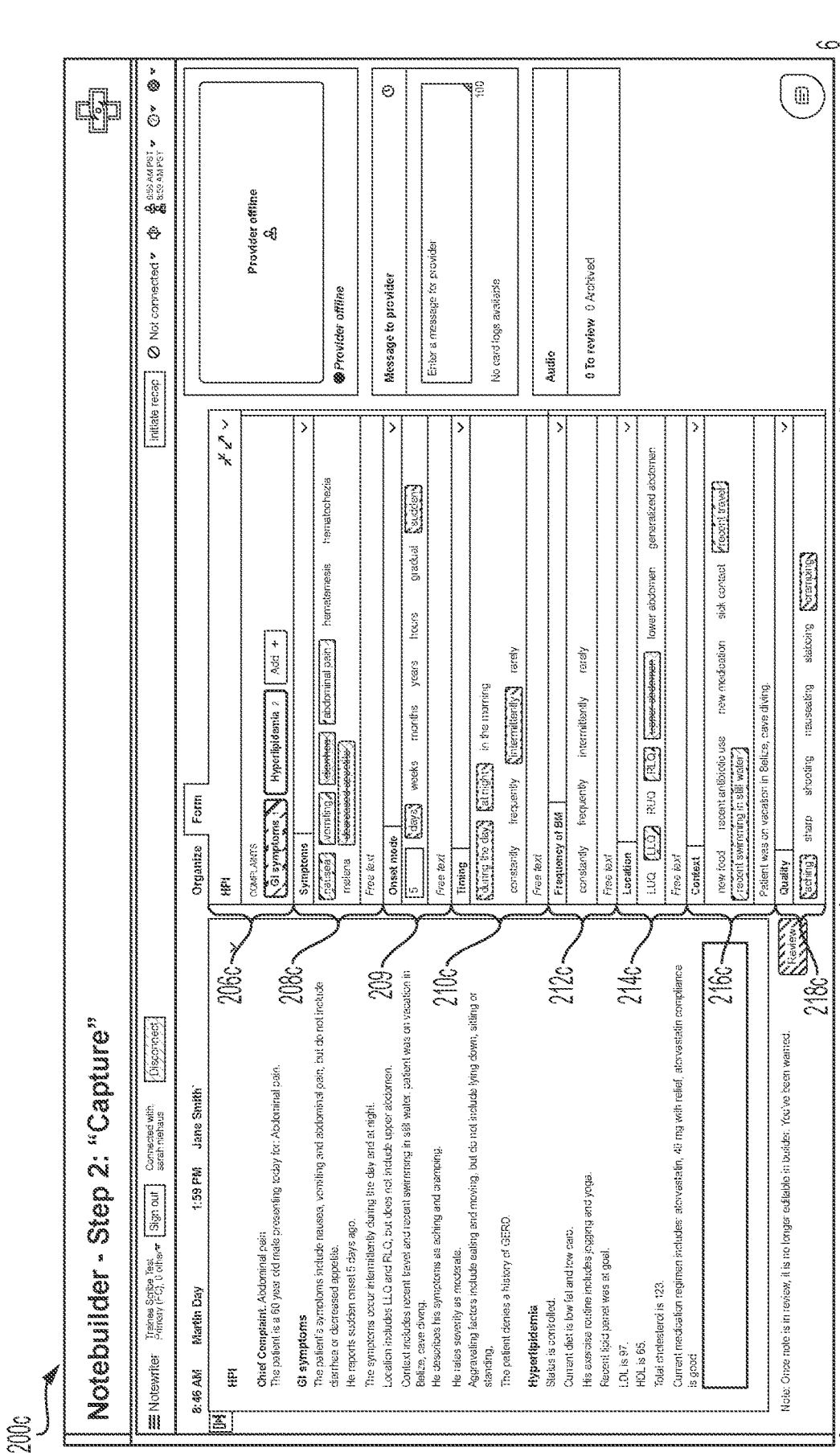

FIG. 2C depicts screen 200c of a graphical user interface 200, in accordance with some embodiments. Screen 200c depicts GUI 200 during the process of capturing of information during a patient visit (e.g., following a set-up/organize stage). As shown in FIG. 2C, a canvas region 202c and a menu region 204c are displayed during the capture process. The description of screen 200c below provides an overview of certain functionalities of the systems and platforms disclosed herein, with aspects of screen 200c that are the same or similar as screen 200a not described or described only briefly, and with corresponding reference numerals used for same/similar portions of the screens (e.g., menu region 204c may share one or more features in common with menu region 204a).

In some embodiments, canvas region 202c may share any one or more features in common with canvas region 202a described above with reference to FIG. 2A; similarly, menu region 204c may share any one or more features in common with menu region 204a described above with reference to FIG. 2A.

In the example of screen 200c in FIG. 2C, screen 200c may be configured to capture information (e.g., symptom information and/or other medical information) related to two complaints: "GI Symptoms" and "Hyperlipidemia," each of which are shown in complaints sub-region 206c. These two complaints may have been indicated by a user at a set-up phase, e.g., using screen 200b. As shown in complaints sub-region 206c, the "GI Symptoms" complaint has been selected by a user (and is accordingly highlighted by being shown in bold); accordingly, the other sub-regions shown in menu region 204c may be sub-regions corresponding to symptom information and other medical information relevant to the "GI Symptoms" complaint. If the user tapped or clicked on the "Hyperlipidemia" complaint button/icon in sub-region 206c, then GUI 200 may replace display of the "GI Symptoms" sub-regions shown in screen 200c with a different set of sub-regions relevant to the hyperlipidemia complaint.

In the example of FIG. 2C, other sub-regions included in menu region 204c may include symptoms sub-region symptoms sub-region 208c, onset mode sub-region 209c, timing sub-region 210c, frequency sub-region 212c, location sub-region 214c, context sub-region 216c, and quality sub-region 218c. The sub-regions 208c-218c may chare one or more features in common with respective sub-regions 208a-218a as described above with reference to screen 200a in FIG. 2A.

In some embodiments, symptoms sub-region 208c may be configured to allow a user to indicate information regarding symptom onset for a patient. In some embodiments, the symptom onset information may be associated by the system with a respective complaint under which the user is working (e.g., "GI symptoms"). As shown, symptoms sub-region 208c includes a free-text field as well as eight option buttons each representing a potential symptom descriptor. As shown, the user has selected three of the options, "nausea," "vomiting," and "abdominal pain"; has deselected two of the options, "diarrhea" and "decreased appetite"; and has left the other three options not selected. Accordingly, the system has generated a natural-language statement regarding the selected and deselected symptom options and displayed said statement in canvas region 202c: "The patient's symptoms include nausea, vomiting, and abdominal pain, but do not include diarrhea or decreased appetite."

In some embodiments, onset sub-region 209c may be configured to allow a user to indicate information regarding symptom onset (e.g., onset mode and/or onset timing) for a patient. In some embodiments, the symptom onset information may be associated by the system with a respective complaint under which the user is working. As shown, onset sub-region 209c includes a free-text field as well as a number-entry field and seven option buttons arranged into two option groups. The option group on the right pertains to onset mode, and the user has selected the option indicating a "sudden" onset mode and left the option indicating a "gradual" onset mode not selected. The option group on the left pertains to onset timing and includes five option buttons and an associated number entry field. As shown, the user has selected the option indicating a number of "days" and has left the other four options not selected; the user has entered t number "5" into the number entry field, thereby specifying an onset timing of five days. In accordance with the options selected and information entered in both option groups, the system has generated a natural-language statement and displayed said statement in canvas region 202c: "He reports sudden onset five days ago."

In some embodiments, timing sub-region 210c may be configured to allow a user to indicate information regarding symptom timing for a patient. In some embodiments, the symptom timing information may be associated by the system with a respective complaint under which the user is working. As shown, timing sub-region 210c includes a free-text field as well as seven option buttons each representing a potential symptom timing descriptor. As shown, the user has selected three of the options—"during the day," "at night," and "intermittently"—and left the other four options not selected. Accordingly, the system has generated a natural-language statement regarding the selected symptom timing option and displayed said statement in canvas region 202c: "The symptoms occur intermittently during the day and at night."

In some embodiments, frequency sub-region 212c may be configured to allow a user to indicate information regarding symptom frequency or the frequency of any other medically-relevant occurrence (e.g., frequency of bowel movements) for a patient. In some embodiments, the frequency information may be associated by the system with a respective complaint under which the user is working. As shown, frequency sub-region 212c includes a free-text field as well as four option buttons each representing a potential frequency descriptor. As shown, the user has left all four options not selected. Accordingly, the system has not generated/displayed a sentence regarding frequency in canvas region 202c.

In some embodiments, location sub-region 214c may be configured to allow a user to indicate information regarding symptom location for a patient. In some embodiments, the symptom location information may be associated by the system with a respective complaint under which the user is working. As shown, location sub-region 214c includes a free-text field as well as seven option buttons each representing a potential frequency descriptor. As shown, the user has selected two of the options, "LLQ" and "RLQ"; deselected one of the options, "upper abdomen"; and left the other four options not selected. Accordingly, the system has generated a natural-language statement regarding the selected and deselected location options and displayed said statement in canvas region 202c: "Location includes LLQ and RLQ, but does not include upper abdomen."

In some embodiments, context sub-region 216c may be configured to allow a user to indicate information regarding contextual information for a patient. In some embodiments, the contextual information may be associated by the system with a respective complaint under which the user is working. As shown, context sub-region 216c includes a free-text field as well as six option buttons each representing a potential frequency descriptor. As shown, the user has selected two of the option buttons—"recent travel" and "recent swimming in still water"—and left the other four options not selected. Accordingly, the system has generated a natural-language statement regarding the selected context options and displayed said statement in canvas region 202c: "Context includes recent travel and recent swimming in still water." Furthermore, the user has typed a sentence into the free text field in sub-region 216c, and the sentence has been appended onto the end of the natural-language statement generated in accordance with the selected input options and displayed in canvas region 202c.

In some embodiments, quality sub-region 218c may be configured to allow a user to indicate information regarding symptom quality for a patient. In some embodiments, the symptom quality information may be associated by the system with a respective complaint under which the user is working. As shown, quality sub-region 218c includes a free-text field as well as six option buttons each representing a potential symptom quality descriptor. As shown, the user has selected two of the option buttons—"aching" and "cramping"—and left the other four options not selected. Accordingly, the system has generated a natural-language statement regarding the selected symptom quality options and displayed said statement in canvas region 202c: "He describes his symptoms as aching and cramping."

In some embodiments, a menu region such as menu region 204c may be configured such that one or more sub-regions, option groups, and/or options may be displayed or suppressed from display in accordance with one or more options selected in the menu region by the user. For example, the system may be configured to automatically display certain options regarding symptoms, symptom characteristics, tests, and/or medication in accordance with symptom information and/or other medical information indicated by the user via selection of one or more options. In some embodiments, the system may be configured to prioritize or deprioritize (e.g., by displaying in a higher position in a list) one or more sub-regions, option groups, and/or options in accordance with one or more options selected in the menu region by the user.

As shown on canvas region 202c, a canvas region may display automatically-generated natural-language statements organized into different sections in accordance with the template being applied. In some embodiments, when a user has indicated more than one complaint for a patient consultation, a canvas region may display separate sections for statements pertaining to the different complaints. In the example of screen 200c, canvas region 202c includes a first section including statements pertaining to the "GI symptoms" complaint and a second section including statements pertaining to the "hyperlipidemia" complaint.

In some embodiments, a user of GUI 200 may be able to edit automatically-generated statements and/or statements generated based on text typed into free-text fields by typing/editing directly on a canvas region such as canvas region 202c.

In some embodiments, GUI 200 may be configured such that, alternatively or additionally to natural-language statements being automatically displayed in canvas region 202c, natural-language statements may be automatically suggested for display in canvas region 202c. For example, the system may suggest a sentence (e.g., by displaying the suggested sentence in another region of the screen or by displaying it in a provisional format such as grayed-out text) that the user may approve for display (or non-provisional display) in canvas region 202c.

Figure 2D:
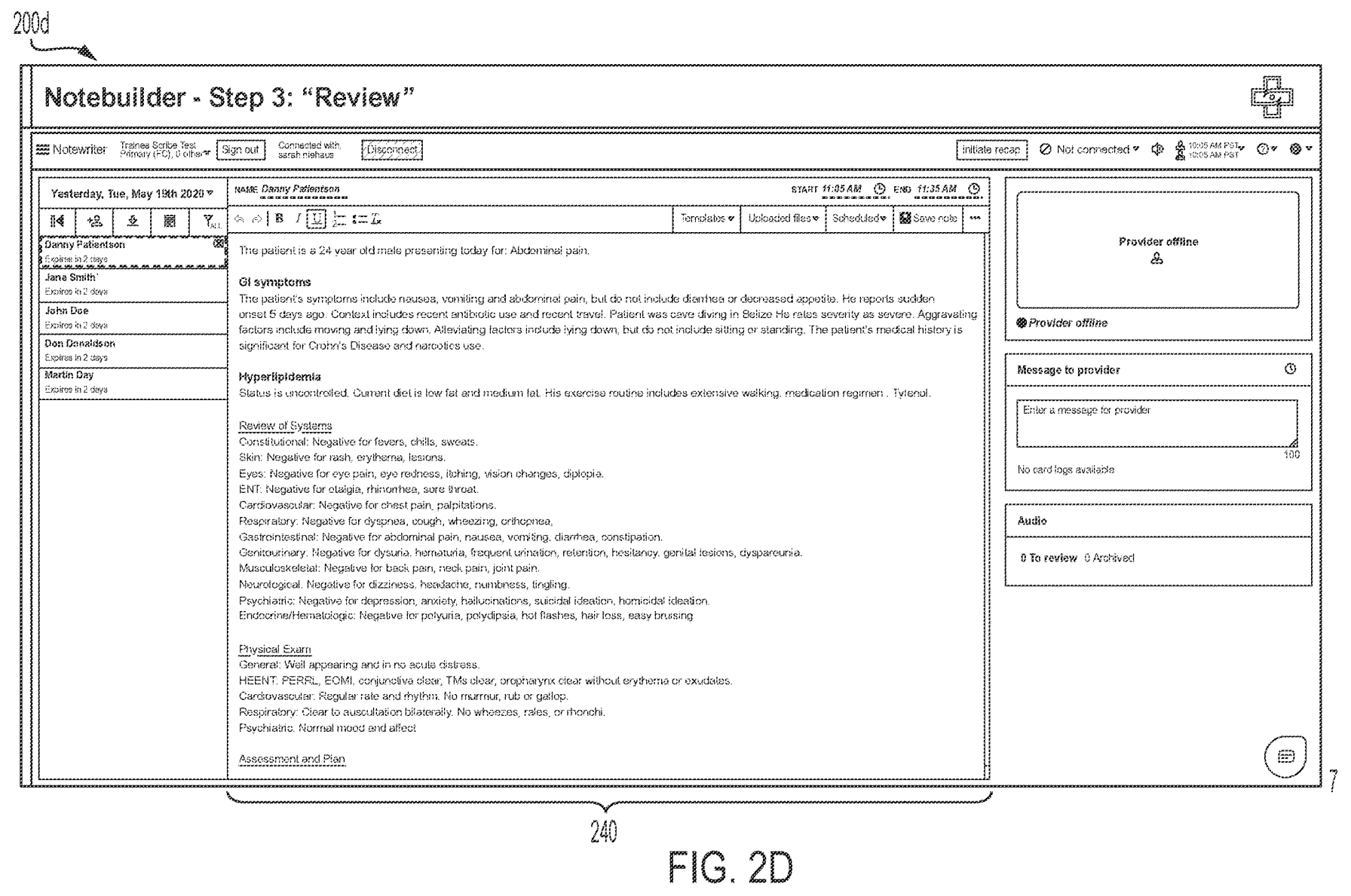

FIG. 2D depicts a screen 200d of a graphical user interface of a natural-language medical record generation platform, in accordance with some embodiments. Screen 200d depicts GUI 200 during the process of reviewing a plurality of natural-language statements generated during a capture stage; after capture, a user may execute one or more inputs to cause GUI 200 to enter a review mode such as the review mode shown by screen 200d. As shown in FIG. 2D, instead of including a canvas portion and a menu portion, screen 200d includes review portion 240.

In some embodiments, a review portion such as review portion 240 may be configured to display the natural-language statements generated based on the inputs received during the capture stage, wherein the statements are displayed on the review portion in a review format. In some embodiments, a review portion may display one or more statements in paragraph form rather than on individual lines, such that the sentences are saved in a unified paragraph form in the electronic health record. In some embodiments, a user of GUI 200 may be able to specify by one or more user-adjustable settings whether or not statements are collapsed from separate lines into paragraph format at the review stage.

In some embodiments, screen 200d may be configured to allow a user to edit one or more of the generated natural-language statements at the review stage, for example by allowing a user to manually execute word-processing inputs into review portion 240 in order to add text, delete text, or modify text displayed in review portion 240. In some embodiments, screen 200d may enable a user to apply one or more automated editing or review tools such as spell-check.

Figure 3:
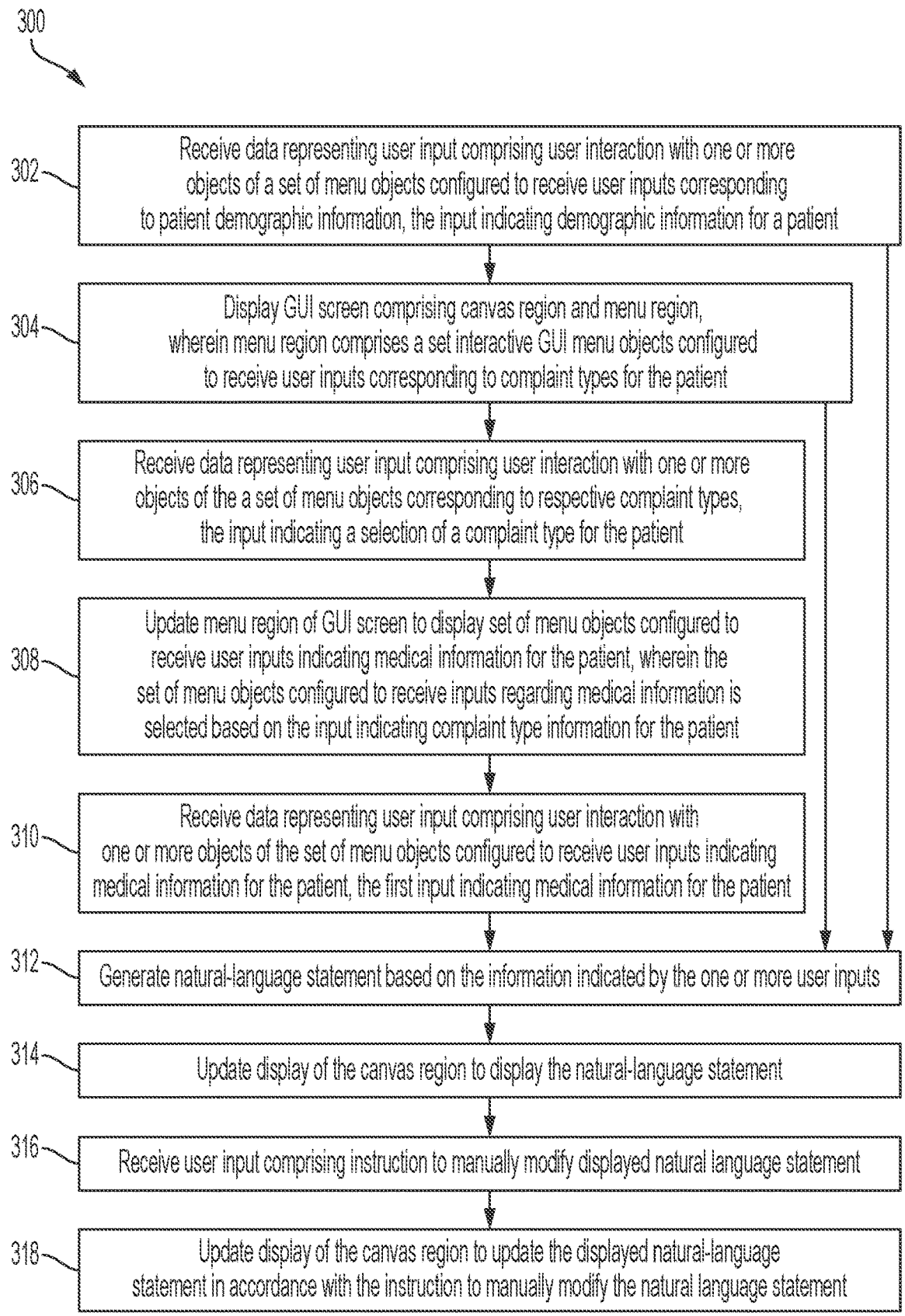
FIG. 3 depicts a flow chart describing a method for providing a natural-language medical record generation platform, in accordance with some embodiments.

FIG. 3 depicts a flow chart describing method 300 for providing a natural-language medical record generation platform, in accordance with some embodiments. In some embodiments, method 300 may be performed by a system for providing a natural-language medical record generation platform, such as system 100 described above with reference to FIG. 1. As described below, method 300 may include providing one or more GUI screens for accepting user inputs regarding patient demographic information, patient complaint information, and/or patient medical information and for displaying and/or editing one or more natural-language statements generated based on the received user inputs. In some embodiments, the one or more GUI screens displayed in method 300 may include (or may share one or more features in common with) one or more of GUI screens 200a-200D described above in FIGS. 2A-2D.

At block 302, in some embodiments, the system may receive data representing a user input comprising a user interaction with one or more objects of a set of objects configured to receive user inputs corresponding to patient demographic information, the user input indicating demographic information for a patient. The system may receive any data representing a user input comprising an indication of patient demographic information. In some embodiments, a user may execute an input indicating patient demographic information by interacting with one or more GUI objects (e.g., text fields, drop-down menus, check-boxes, selectable and/or deselectable buttons/icons).

In some embodiments, the receipt of inputs indicating patient demographic information at block 302 may include receiving inputs executed by a user via a user interface screen configured to accept inputs regarding patient demographic information, such as GUI screen 200b described above with respect to FIG. 2B. For example, a user may indicate patient demographic information by inputting information into demographic information region 230 of GUI screen 200b; a user may type information such as a patient name into a text field, may indicate information such as patient date of birth by using a drop-down menu, and/or may indicate patient gender by selecting one or more selectable icons.

In some embodiments, the system may be configured to determine which menu options to display to a user based on the indicated demographic information, such as by configuring a template such that GUI options available to the user are selected and presented based on patient age, gender, or other demographic information. Furthermore, as explained further below, the system may configure the structure of one or more natural-language statements based on the indicated demographic information, such as by inserting the patient's name into the statement and/or by configuring pronouns in the statement according to the indicated gender for the patient.

At block 304, in some embodiments, the system may display a GUI screen comprising a canvas region and a menu region, wherein the menu region comprises a set of interactive GUI menu objects configured to receive user inputs corresponding to complaint types for the patient. In some embodiments, the displayed GUI screen may be (or may share one or more features in common with) GUI screen 200c including canvas region 202c and menu region 204c, as described above with respect to FIG. 2C. The set of interactive GUI menu objects configured to receive user inputs corresponding to complaint types may include (or may share one or more features in common with) the selectable/deselectable icons indicating patient complaints in complaints sub-region 206c. In accordance with a user selecting, adding, or removing a complaint type by interacting with one or more of the icons in complaints sub-region 206c (and/or in accordance with a user otherwise indicating one or more complaints via interaction with the GUI), the system may responsively cause display of one or more GUI objects configured to receive inputs regarding medical information pertinent to an indicated complaint.

At block 306, in some embodiments, the system may receive data representing user input comprising user interaction with one or more objects of the set of menu objects corresponding to respective complaint types, the input indicating a selection of a complaint type for the patient. In the example of FIG. 2C, the user has selected the icon for the "GI Symptoms" complaint, as indicated by the fact that the "GI Symptoms" icon is shown in bold typeface.

At block 308, in some embodiments, the system may update the menu region of the GUI screen to display a set of menu objects configured to receive user inputs indicating medical information for the patient, wherein the set of menu objects configured to receive inputs regarding medical information is selected based on the input indicating complaint type for the patient. The system may select the menu objects that are displayed by selecting from among a plurality of predetermined sets of one or more menu objects, each of the plurality of sets of one or more menu objects corresponding to a different respective complaint. In some embodiments, the system may select which menu objects are displayed based on known patient information, demographic information, practitioner information, and/or a user indication of a specialty, a healthcare system, a payer, and/or a clinician.

In some embodiments, the system may display one or more GUI objects and/or GUI regions configured to accept inputs regarding patient medical informant pertinent to an indicated complaint. In some embodiments, the indicated complaint may be indicated by selection of one or more GUI objects configured to receive inputs regarding complaint types as described above.

In some embodiments, the set of menu objects configured to receive inputs regarding medical information may include one or more text fields, drop-down menus, check-boxes, selectable and/or deselectable buttons/icons. In some embodiments, the system may display GUI objects for accepting inputs regarding medical information organized into groups of GUI objects, such as the selectable/deselectable icons organized into various sub-regions and/or into one or more separate object groups therein, as shown in the example of FIG. 2C.

In the example of FIG. 2C, the user has selected the icon for the "GI Symptoms" complaint in complaints sub-region 206c, and the system has accordingly displayed sub-regions 208c-218c each including one or more GUI objects configured to accept user inputs regarding medical information pertinent to the "GI Symptoms" complaint. The system may automatically determine which sub-regions, which GUI objects therein, and/or which GUI object groups therein are to be displayed to the user based at least in part on a complaint indicated by the user.

In some embodiments, the sub-regions, GUI objects, and/or GUI object groups configured to accept inputs regarding patient medical information may further be automatically determined and selected by the system on the basis of indicated patient demographic information (e.g., information indicated at block 302 and/or via a demographic information GUI region such as demographic information region 230 of GUI screen 200b. In some embodiments, the sub-regions, GUI objects, and/or GUI object groups configured to accept inputs regarding patient medical information may further be automatically determined and selected by the system on the basis of previously-indicated medical information for the patient, such that one or more indications of medical information (e.g., inputs made by the user to menu region 204c via one or more of sub-regions 208c-218c) may cause the system to automatically and dynamically update the displayed GUI objects for indicating medical information. For example, if a user makes an indication of medical information that the system determines may exclude the possibility of another line of inquiry being relevant, then options pertaining to that line of inquiry may be automatically suppressed from display by the system.

In some embodiments, the displayed menu objects may be arranged into one or more subsets, such as subsets relating to respective potential symptoms, respective potential symptom onset characterizations, respective potential symptom timing information, respective potential symptom frequency, respective potential symptom locations, respective potential contextual information, respective potential symptom quality, respective potential prior medical conditions, respective potential diagnoses, represents a respective potential current medications, respective potential medications to be prescribed, respective potential current treatments, and/or respective potential treatment to be prescribed.

At block 310, in some embodiments, the system may receive data representing a user input comprising a user interaction with one or more objects of the set of menu objects configured to receive user inputs indicating medical information for the patient, the first input indicating medical information for the patient. For example, as described above with reference to FIG. 2C, a user of the system may enter text into one or more fields, select one or more drop-down menu items, and/or select or deselect one or more selectable/deselectable icons/buttons.

At block 312, in some embodiments, the system may generate a natural-language statement based on the information indicated by the one or more user inputs. In some embodiments, the natural-language statement generated may be generated based on a natural-language statement structure indicated by one or more templates applied by the system based on indicated patient demographic information (e.g., as indicated at block 302), indicated complaint information (e.g., as indicated at block 306), and/or indicated patient medical information (e.g., as indicated at block 312). In some embodiments, generating the natural-language statement based on the medical information indicated by the first user input comprises inserting a text string associated with the indicated medical information into a predefined syntactical structure. In some embodiments, the natural-language statement may be generated based on multiple user inputs indicating multiple aspects of patient demographic and/or medical information.

In some embodiments, in addition to or alternately to a natural-language statement being generated by the system based on one or more selections of options by a user, a natural language statement may be generated by the system based in whole or in part on text entered by a user into a text field. For example, the system may insert a character string entered into a text field by a user into a predetermined natural-language sentence structure. In some embodiments, the system may insert a character string entered into a text field by a user into a predetermined natural-language paragraph structure as a complete sentence.

At block 314, in some embodiments, the system may update display of the canvas region to display the natural-language statement. As show in the example of FIG. 2C, various natural-language statements based on user inputs made in menu region 204c are displayed in canvas region 202c.

At block 316, in some embodiments, the system may receive a user input comprising an instruction to manually modify the displayed natural-language statement. At block 318, in some embodiments, the system may update display of the canvas region to update the displayed natural-language statement in accordance with the instruction to manually modify the natural-language statement.

In some embodiments, an instruction to manually modify one or more automatically-generated natural language statements displayed on a canvas region may be made by a user directly via a canvas region of a GUI or via another region/portion/object of a GUI including the canvas region. For example, in some embodiments, a user may be permitted to type directly into a canvas region to add to, delete from, or modify portions of an automatically-generated natural language statement displayed therein.

In some embodiments, a user may be permitted to manually modify a natural-language statement displayed at a review screen of a GUI, distinct from a canvas region, such as review portion 240 of screen 200d described above with respect to FIG. 2D. In some embodiments, functionality for manually revising a natural-language statement at a review screen may be provided additionally or alternatively to functionality for revising a natural-language statement directly in a canvas portion such as portion 202c of screen 200c.

Figure 4A:
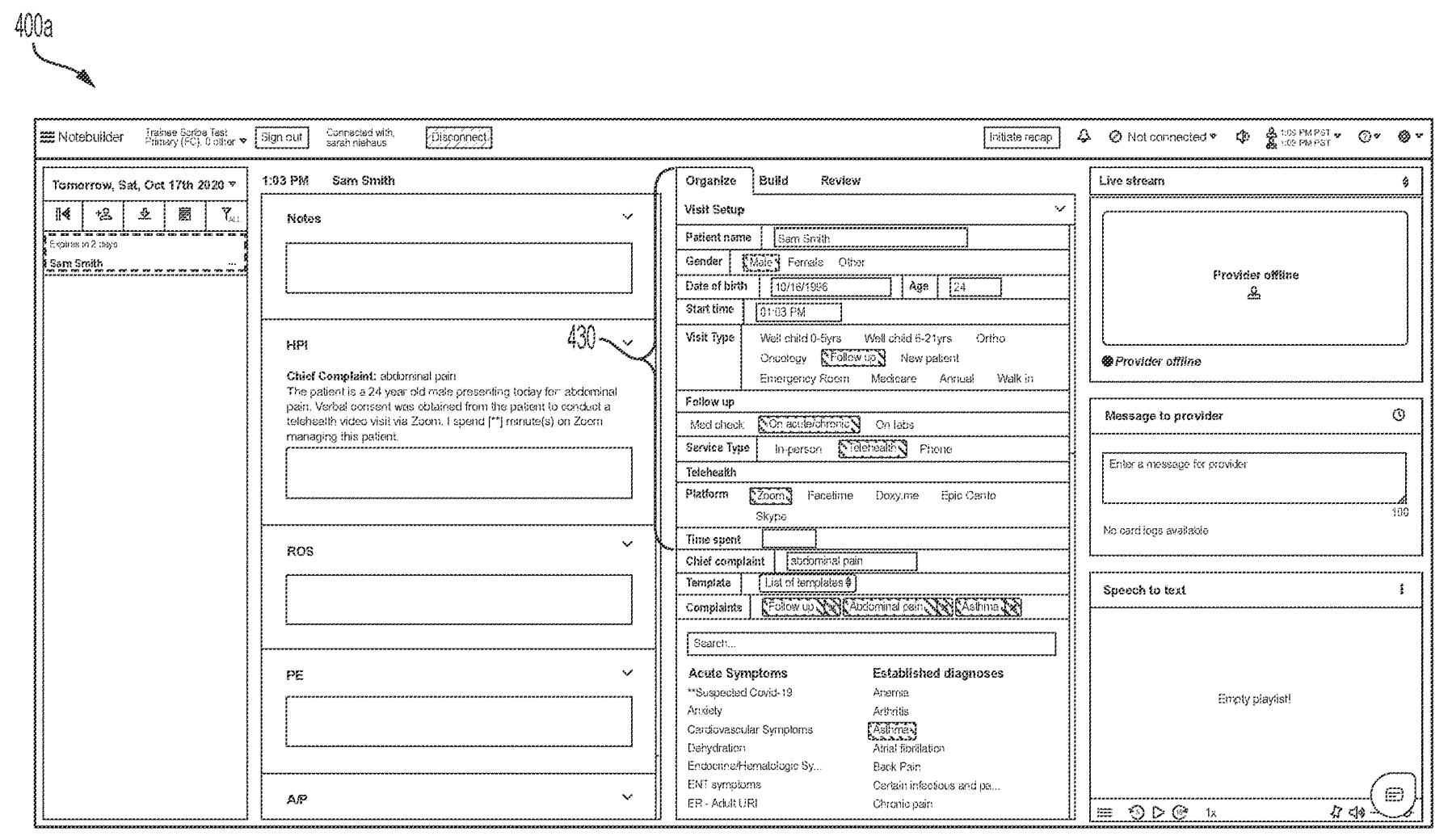
Figure 4B:
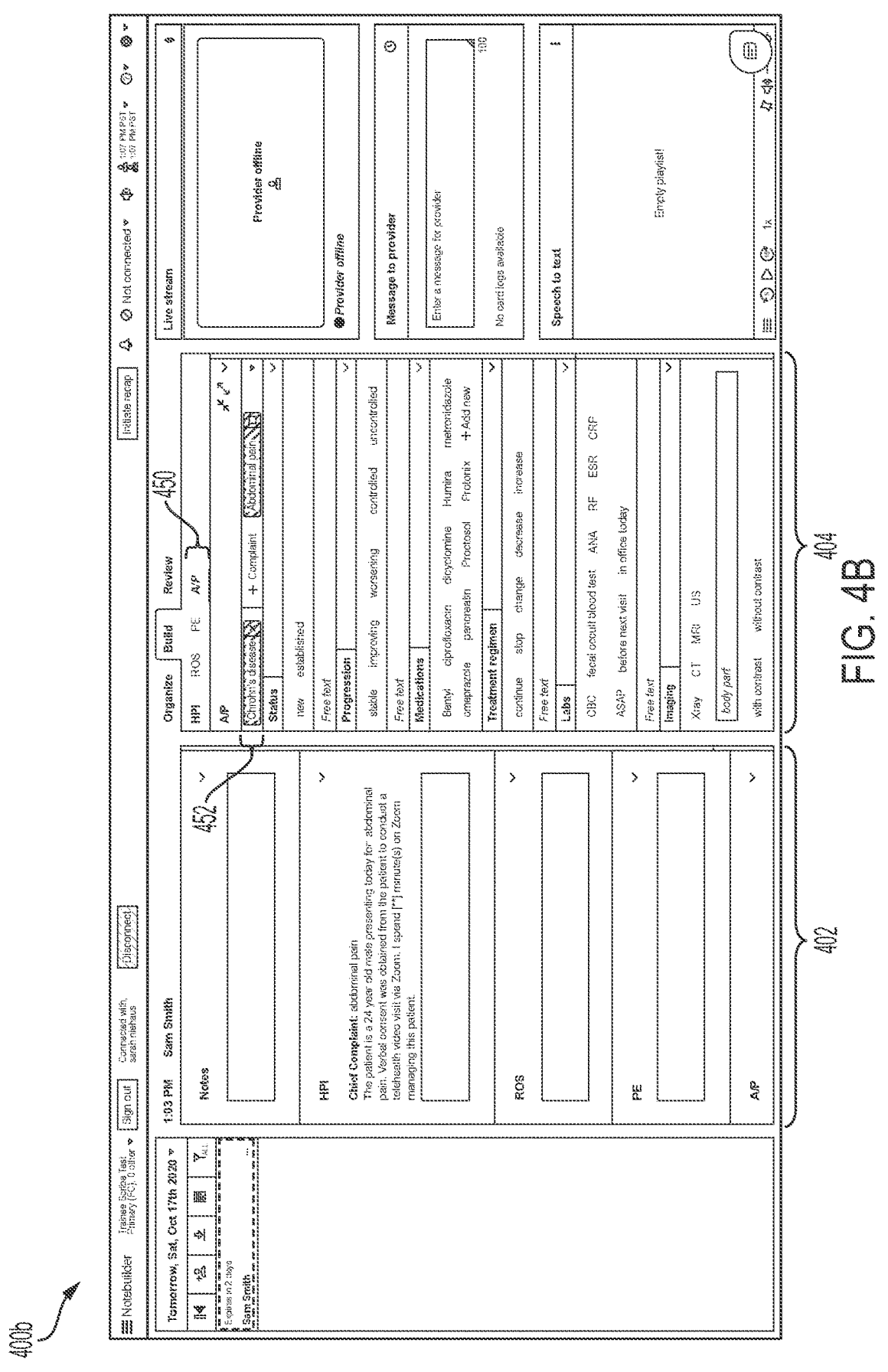

FIGS. 4A and 4B depict respective screens 400a and 400b of graphical user interface 400 of a natural-language medical record generation platform, in accordance with some embodiments. In some embodiments, GUI 400 may share any one or more characteristics in common with GUI 200 described above. Various functionalities of the systems and platforms disclosed herein are described below with reference to GUI screens 400a and 400b, with particular attention given to differences over features of GUI 200 as described above.

FIG. 4A depicts screen 400a of a graphical user interface 400, in accordance with some embodiments. Screen 400a depicts GUI 400 during the process of organizing or setting up the interface for capture of information during a patient visit. In some embodiments, screen 400a may share any one or more features in common with screen 200b of GUI 200, described above with reference to FIG. 2B.

Screen 400a may differ from screen 200b in that demographic information region 430 may comprise one or more additional GUI objects and be configured to accept one or more additional types of patient visit information as compared to demographic information region 230 of screen 200b. As shown in FIG. 4A, region 430 may comprise a set of selectable and/or deselectable icons/buttons for indicating a "visit type"; a set of selectable and/or deselectable icons/buttons for indicating a type of follow-up; a set of selectable and/or deselectable icons/buttons for indicating a service type (e.g., the type of patient visit being performed); a set of selectable and/or deselectable icons/buttons for indicating a platform via which the patient visit is being performed; and a field for indicating an amount of time spent on the patient visit.

In some embodiments, one or more of the sets of selectable and/or deselectable icons/buttons in region 430 may be displayed and/or hidden responsively to a selection made or other input executed by a user. For example, the options for indicating a follow-up type may be displayed in response to the user selecting the "follow-up" visit type icon/button. The options for indicating a platform type may be displayed in response to the user selecting the "telehealth" service type icon/button.

In some embodiments, the system may be configured such that GUI 400 requires selection of at least one option for a visit type. In some embodiments, the system may be configured such that GUI 400 requires selection of exactly one option for a visit type (or of at least one and no more than a predetermined maximum number of visit type options). In some embodiments, the selected "visit type" option may be used by the system to configure the template used to select and display one or more options for indicating medical information for a patient at a screen of GUI 400 for capturing medical information during the patient visit. In this way, the system may treat "visit type" as a special class of complaint types (e.g., a sub-class of complaint types), in that the system may use an indicated visit type in order to select sub-regions and GUI objects that are medically-relevant to the indicated visit-type. (In some embodiments, the "visit type" options may differ from "complaint" options in that the system may draw from different information sources to populate the available visit type options versus those used to populate available complaints.)

In some embodiments, one or more of the options selected (and/or user inputs otherwise indicated) in region 430 may be used to generate a natural-language statement for display in a canvas region of GUI 400 (e.g., a sentence may be generated stating the service type of the visit).

FIG. 4B depicts screen 400b of a graphical user interface 400, in accordance with some embodiments. Screen 400b depicts GUI 400 during the process of capturing of information during a patient visit (e.g., following a set-up/organize stage). In some embodiments, screen 400b may share any one or more features in common with screen 200a of GUI 200, described above with reference to FIG. 2A, and/or with screen 200c, described above with reference to FIG. 2C.

Screen 400a may include canvas region 402 and menu region 404, which may share one or more characteristics in common with canvas regions and menu regions, respectively, as described elsewhere herein. Screen 400a may differ from screens 200a and/or 200c in that menu region 404 may include note section navigation icons 450. As shown in FIG. 4B, navigation icons 450 may include an "HPI" (history of present illness) icon, a "ROS" (review of systems) icon, a "PE" (physical examination) icon, and an "A/P" (assessment/plan) icon. In some embodiments, selecting any one of the icons (e.g., by clicking or tapping the icon) in note section navigation icons 450 may cause GUI 400 to navigate to a corresponding portion of the note displayed in canvas region 402 and/or to display corresponding menu options in menu region 404. Thus, by clicking different navigation icons, a user may quickly navigate between different sections of the note and cause quick display of both the generated natural language note-contents and the GUI objects for inputting information relevant to that section of the note. In some embodiments, any one or more of the different sections of the interface for preparing note contents (e.g., HPI section, ROS section, PE section, A/P section) may share any one or more characteristics in common with one another.

In some embodiments, one or more GUI objects (e.g., selectable icons/buttons) splayed in a menu region of a GUI such as GUI 400 (or GUI 200) may be displayed in accordance with clinician preference and/or other back-end configurations. In some embodiments, one or more GUI options displayed in menu region 404 when the "ROS" or "PE" navigation icons are selected may be determined according to clinician preferences managed by back-end system configuration (e.g., rather than interactively/dynamically selected by a user of GUI 400).

As shown in FIG. 4B, menu region 404 may include A/P complaint selection sub-region 452. An A/P complaint selection sub-region may be a GUI region in which a user may input an indication of a complaint for which the A/P section of the menu region 404 is to be filled out. In some embodiments, a clinician or practitioner may have different assessment/plan information to enter for different patient complaints, or may intend to enter overlapping common assessment/plan information for two or more patient complaints. Accordingly, A/P complaint selection sub-region 452 may be auto-populated with options for selecting one or more complaints that were previously indicated at the setup stage (and/or for adding one or more new complaints) such that the user may flexibly indicate one or more complaints for which the user intends to enter assessment/plan information. In some embodiments, the A/P complaint selection sub-region 452 may additionally or alternatively allow a user to indicate a diagnosis. Indication of one or more complaints and/or diagnoses in sub-region 452 may cause GUI 400 to display one or more GUI objects in the A/P section of region 404 for entering information about the indicated complaints and/or diagnoses.

Figure 5:
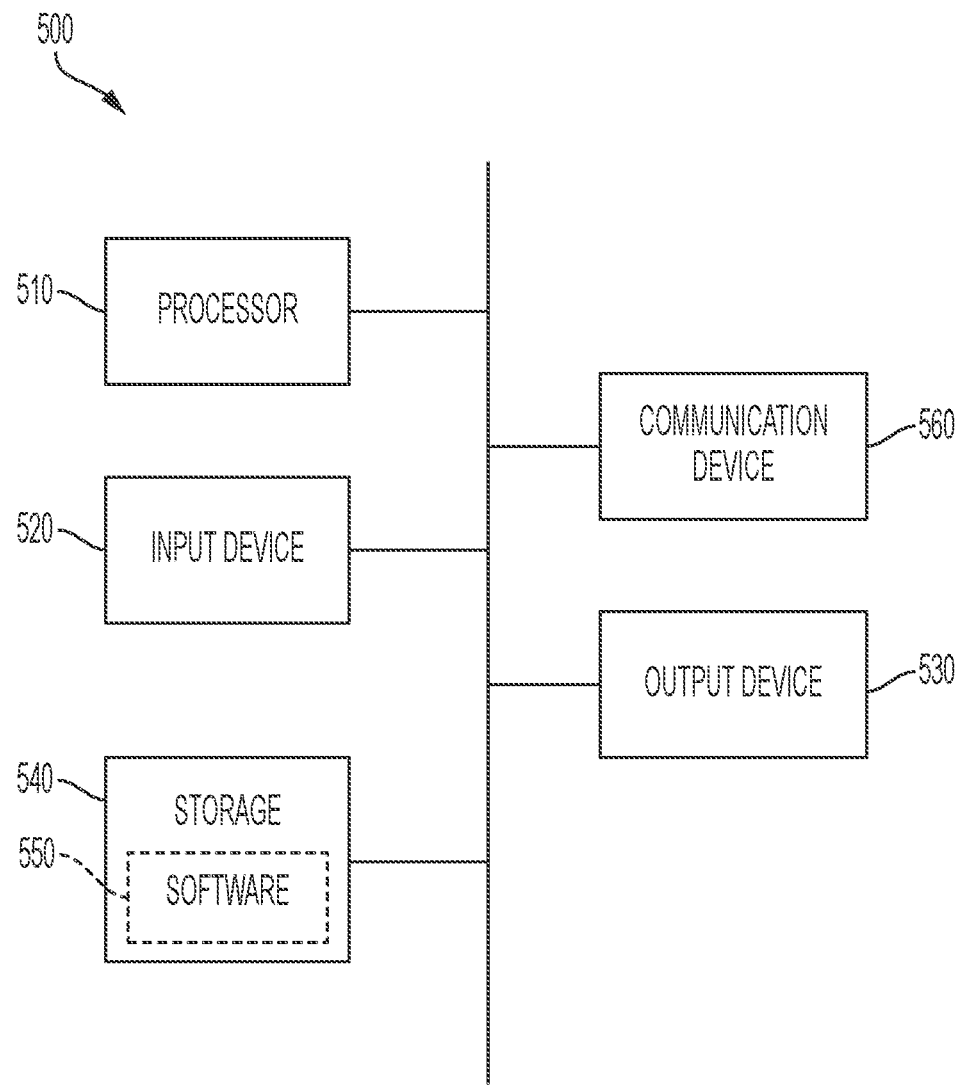
FIG. 5 depicts a computer, in accordance with some embodiments.

FIG. 5 illustrates an example of a computer, according to some embodiments. Computer 500 can be a component of a bioelectrical sensor system according to the systems and methods described above, such as system 100 of FIG. 1. In some embodiments, computer 500 may execute a method for automatically generating natural-language entries for electronic health records and/or for configuring systems and graphical user interfaces for automatically generating natural-language entries for electronic health records.

Computer 500 can be a host computer connected to a network. Computer 500 can be a client computer or a server. As shown in FIG. 5, computer 500 can be any suitable type of microprocessor-based device, such as a personal computer, workstation, server, or handheld computing device, such as a phone or tablet. The computer can include, for example, one or more of processor 510, input device 520, output device 530, storage 540, and communication device 560. Input device 520 and output device 530 can correspond to those described above and can either be connectable or integrated with the computer.

Input device 520 can be any suitable device that provides input, such as a touch screen or monitor, keyboard, mouse, or voice-recognition device. Output device 530 can be any suitable device that provides an output, such as a touch screen, monitor, printer, disk drive, or speaker.

Storage 540 can be any suitable device that provides storage, such as an electrical, magnetic, or optical memory, including a random access memory (RAM), cache, hard drive, CD-ROM drive, tape drive, or removable storage disk. Communication device 560 can include any suitable device capable of transmitting and receiving signals over a network, such as a network interface chip or card. The components of the computer can be connected in any suitable manner, such as via a physical bus or wirelessly. Storage 540 can be a non-transitory computer-readable storage medium comprising one or more programs, which, when executed by one or more processors, such as processor 510, cause the one or more processors to execute methods described herein.

Software 550, which can be stored in storage 540 and executed by processor 510, can include, for example, the programming that embodies the functionality of the present disclosure (e.g., as embodied in the systems, computers, servers, and/or devices as described above). In some embodiments, software 550 can include a combination of servers such as application servers and database servers.

Software 550 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 540, that can contain or store programming for use by or in connection with an instruction execution system, apparatus, or device.

Software 550 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include but is not limited to, an electronic, magnetic, optical, electromagnetic, or infrared wired or wireless propagation medium.

Computer 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 500 can implement any operating system suitable for operating on the network. Software 550 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The following is a non-limiting list of embodiments, any of which may be combined in whole or in part with one another and/or in whole or in part with any other aspects or features disclosed herein:

1. A system for generating a natural-language statement for a healthcare record, the system comprising one or more processors configured to cause the system to:
   display a graphical user interface comprising a canvas region and a menu region, wherein menu region comprises a first set of one or more interactive graphical user interface menu objects configured to receive user inputs corresponding to medical information; and
   receive data representing a first user input comprising user interaction with one or more of the first set of menu objects, the first input indicating medical information for a patient;
   in accordance with the first user input:
      generate a natural-language statement based on the medical information indicated by the first user input; and
      update display of the canvas region to display the natural-language statement.

2. The system of embodiment 1, wherein generating the natural-language statement based on the medical information indicated by the first user input comprises inserting a text string associated with the indicated medical information into a predefined syntactical structure.

3. The system of any one of embodiments 1-2, wherein the natural-language statement is generated based on the first input and based on one or more additional inputs indicating additional medical information for the patient.

4. The system of any one of embodiments 1-3, wherein one or more processors configured to cause the system to store data representing a healthcare record, the data comprising the generated natural-language statement.

5. The system of any one of embodiments 1-4, wherein:
   the menu region comprises a second set of one or more menu objects configured to receive user inputs corresponding to demographic information;
   the one or more processors are configured to cause the system to receive data representing a second user input comprising user interaction with one or more of the second plurality of menu objects, the second input indicating patient demographic information for the patient; and
   generating the natural language statement is performed in accordance with the second user input.

6. The system of any one of embodiments 1-5, wherein:
the menu region comprises a third set of one or more menu objects configured to receive user inputs corresponding to complaint information;
the one or more processors are configured to cause the system to receive data representing a third user input comprising user interaction with one or more of the third plurality of menu objects, the third input indicating complaint information for the patient; and
wherein the first set of one or more menu objects are selected by the system for display in the interface based on the complaint information indicated by the third input.

7. The system of embodiment 6, wherein selecting the first set of one or more menu objects comprises selecting from among a plurality of predetermined sets of one or more menu objects, each of the plurality of sets of one or more menu objects corresponding to a different respective complaint.

8. The system of any one of embodiments 6-7, wherein selecting the first set of one or more menu objects is performed on the basis of indication by a user of one or more of a specialty, a healthcare system, a payer, and a clinician.

9. The system of any one of embodiments 1-8, wherein:
the first set of one or more menu objects comprises a first subset of menu objects, wherein each of the menu objects of the first subset represents a respective potential symptom; and
the first input comprises a selection of one or more of the menu objects of the first subset representing a symptom of the patient.

10. The system of any one of embodiments 1-9, wherein:
the first set of one or more menu objects comprises a second subset of menu objects, wherein each of the menu objects of the second subset represents a respective potential symptom onset characterization; and
the first input comprises a selection of one or more of the menu objects of the second subset representing a symptom onset characterization of the patient.

11. The system of any one of embodiments 1-10, wherein:
the first set of one or more menu objects comprises a third subset of menu objects, wherein each of the menu objects of the third subset represents a respective potential symptom timing information; and
the first input comprises a selection of one or more of the menu objects of the third subset representing symptom timing information of the patient.

12. The system of any one of embodiments 1-11, wherein:
the first set of one or more menu objects comprises a fourth subset of menu objects, wherein each of the menu objects of the fourth subset represents a respective potential symptom frequency; and
the first input comprises a selection of one or more of the menu objects of the fourth subset representing a symptom frequency of the patient.

13. The system of any one of embodiments 1-12, wherein:
the first set of one or more menu objects comprises a fifth subset of menu objects, wherein each of the menu objects of the fifth subset represents a respective potential symptom locations; and
the first input comprises a selection of one or more of the menu objects of the fifth subset representing a symptom location of the patient.

14. The system of any one of embodiments 1-13, wherein:
the first set of one or more menu objects comprises a sixth subset of menu objects, wherein each of the menu objects of the sixth subset represents a respective potential contextual information; and
the first input comprises a selection of one or more of the menu objects of the sixth subset representing contextual information of the patient.

15. The system of any one of embodiments 1-14, wherein:
the first set of one or more menu objects comprises a seventh subset of menu objects, wherein each of the menu objects of the seventh subset represents a respective potential symptom quality; and
the first input comprises a selection of one or more of the menu objects of the seventh subset representing a symptom quality of the patient.

16. The system of any one of embodiments 1-15, wherein:
the first set of one or more menu objects comprises an eighth subset of menu objects, wherein each of the menu objects of the eighth subset represents a respective potential prior medical condition; and
the first input comprises a selection of one or more of the menu objects of the eighth subset representing a prior medical condition of the patient.

17. The system of any one of embodiments 1-16, wherein:
the first set of one or more menu objects comprises a ninth subset of menu objects, wherein each of the menu objects of the ninth subset represents a respective potential current medication; and
the first input comprises a selection of one or more of the menu objects of the ninth subset representing a current medication of the patient.

18. The system of any one of embodiments 1-17, wherein:
the first set of one or more menu objects comprises a tenth subset of menu objects, wherein each of the menu objects of the tenth subset represents a respective potential medication to be prescribed; and
the first input comprises a selection of one or more of the menu objects of the tenth subset representing a medication to be prescribed for the patient.

19. The system of any one of embodiments 1-18, wherein:
the first set of one or more menu objects comprises an eleventh subset of menu objects, wherein each of the menu objects of the eleventh subset represents a respective potential treatment to be prescribed; and
the first input comprises a selection of one or more of the menu objects of the eleventh subset representing a treatment to be prescribed for the patient.

20. The system of any one of embodiments 1-19, wherein:
the first set of one or more menu objects comprises a first field configured to accept entry of character strings;
the first input comprises entry of a first character string into the first field; and
generating the natural-language statement based on the medical information indicated by the first user input comprises inserting the character string into a predetermined natural-language sentence structure.

21. The system of any one of embodiments 1-20, wherein:
the first set of one or more menu objects comprises a second field configured to accept entry of character strings;
the first input comprises entry of a second character string into the second field; and
generating the natural-language statement based on the medical information indicated by the first user input comprises inserting the character string into a predetermined natural-language paragraph structure as a complete sentence.
22. The system of any one of embodiments 1-21, wherein the one or more processors are configured to cause the system to, in accordance with the first user input, dynamically update the menu region.
23. The system of any one of embodiments 1-22, wherein the one or more processors are configured to cause the system to:
    detect a fourth user input comprising an instruction to manually modify the natural-language statement displayed in the canvas region;
    in response to detecting the fourth user input, update the displayed natural-language statement displayed in the canvas region.
24. The system of any one of embodiments 1-23, wherein:
    displaying the natural-language statement in the canvas region comprises displaying the natural-language statement using a first format; and
    the one or more processors are configured to cause the system to display a review screen on which the natural-language statement is displayed using a second format.
25. The system of any one of embodiments 1-24, wherein the one or more processors are configured to cause the system to capture and store metadata representing the first input.
26. The system of any one of embodiments 1-25, wherein updating display of the canvas region to display the natural-language statement is performed automatically in response to detection of the first user input.
27. The system of any one of embodiments 1-26, wherein the system is configured such that only one menu object of the first set of menu objects are able to be selected at once.
28. The system of any one of embodiments 1-27, wherein the system is configured such that multiple menu objects of the first set of menu objects are able to be selected at once.
29. The system of any one of embodiments 1-28, wherein the system is configured such that one or more of the menu objects is able to be toggled between two or more states selected from: positively indicated, negatively indicated, neither positively nor negatively indicated.
30. A non-transitory computer-readable storage medium storing instructions for generating a natural-language statement for a healthcare record, the instructions configured to be executed by a system comprising one or more processors to cause the system to:
    display a graphical user interface comprising a canvas region and a menu region, wherein menu region comprises a first set of one or more interactive graphical user interface menu objects configured to receive user inputs corresponding to medical information; and
    receive data representing a first user input comprising user interaction with one or more of the first set of menu objects, the first input indicating medical information for a patient;
    in accordance with the first user input:
        generate a natural-language statement based on the medical information indicated by the first user input; and
        update display of the canvas region to display the natural-language statement.
31. A method for generating a natural-language statement for a healthcare record, the method performed at a system comprising one or more processor, the method comprising:
    displaying a graphical user interface comprising a canvas region and a menu region, wherein menu region comprises a first set of one or more interactive graphical user interface menu objects configured to receive user inputs corresponding to medical information; and
    receiving data representing a first user input comprising user interaction with one or more of the first set of menu objects, the first input indicating medical information for a patient;
    in accordance with the first user input:
        generating a natural-language statement based on the medical information indicated by the first user input; and
        updating display of the canvas region to display the natural-language statement.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A system for generating a natural-language statement for a healthcare record, the system comprising one or more processors configured to cause the system to:
display a graphical user interface comprising a canvas region and a menu region, wherein the menu region comprises a first set of one or more interactive graphical user interface menu objects configured to receive user inputs corresponding to medical information, wherein one or more of the menu objects is able to be toggled between two or more states selected from: positively indicated, negatively indicated, neither positively nor negatively indicated, and the menu objects in the menu region are displayed in accordance with one or more templates selected by a user of the graphical user interface, the one or more templates controlling the menu objects that are displayed in the menu region and an order in which the menu objects are displayed in the menu region; and
receive data representing a first user input comprising user interaction with one or more of the first set of menu objects, the first input indicating medical information for a patient;
in accordance with the first user input:
generate a natural-language statement based on the medical information indicated by the first user input and in accordance with the one or more templates selected by the user of the graphical user interface; and
update display of the canvas region to display the natural-language statement.

2. The system of claim 1, wherein generating the natural-language statement based on the medical information indicated by the first user input comprises inserting a text string associated with the indicated medical information into a predefined syntactical structure.

3. The system of claim 1, wherein the natural-language statement is generated based on the first input and based on one or more additional inputs indicating additional medical information for the patient.

4. The system of claim 1, wherein one or more processors configured to cause the system to store data representing a healthcare record, the data comprising the generated natural-language statement.

5. The system of claim 1, wherein:
the menu region comprises a second set of one or more menu objects configured to receive user inputs corresponding to demographic information;
the one or more processors are configured to cause the system to receive data representing a second user input comprising user interaction with one or more of the second plurality of menu objects, the second input indicating patient demographic information for the patient; and
generating the natural language statement is performed in accordance with the second user input.

6. The system of claim 1, wherein:
the menu region comprises a third set of one or more menu objects configured to receive user inputs corresponding to complaint information;
the one or more processors are configured to cause the system to receive data representing a third user input comprising user interaction with one or more of the third plurality of menu objects, the third input indicating complaint information for the patient; and
wherein the first set of one or more menu objects are selected by the system for display in the interface based on the complaint information indicated by the third input.

7. The system of claim 6, wherein selecting the first set of one or more menu objects comprises selecting from among a plurality of predetermined sets of one or more menu objects, each of the plurality of sets of one or more menu objects corresponding to a different respective complaint.

8. The system of claim 6, wherein selecting the first set of one or more menu objects is performed on the basis of indication by a user of one or more of a specialty, a healthcare system, a payer, and a clinician.

9. The system of claim 1, wherein:
the first set of one or more menu objects comprises a first subset of menu objects, wherein each of the menu objects of the first subset represents a respective potential symptom; and
the first input comprises a selection of one or more of the menu objects of the first subset representing a symptom of the patient.

10. The system of claim 1, wherein:
the first set of one or more menu objects comprises a second subset of menu objects, wherein each of the menu objects of the second subset represents a respective potential symptom onset characterization; and
the first input comprises a selection of one or more of the menu objects of the second subset representing a symptom onset characterization of the patient.

11. The system of claim 1, wherein:
the first set of one or more menu objects comprises a third subset of menu objects, wherein each of the menu objects of the third subset represents a respective potential symptom timing information; and
the first input comprises a selection of one or more of the menu objects of the third subset representing symptom timing information of the patient.

12. The system of claim 1, wherein:
the first set of one or more menu objects comprises a fourth subset of menu objects, wherein each of the menu objects of the fourth subset represents a respective potential symptom frequency; and
the first input comprises a selection of one or more of the menu objects of the fourth subset representing a symptom frequency of the patient.

13. The system of claim 1, wherein:
the first set of one or more menu objects comprises a fifth subset of menu objects, wherein each of the menu objects of the fifth subset represents a respective potential symptom locations; and
the first input comprises a selection of one or more of the menu objects of the fifth subset representing a symptom location of the patient.

14. The system of claim 1, wherein:
the first set of one or more menu objects comprises a sixth subset of menu objects, wherein each of the menu objects of the sixth subset represents a respective potential contextual information; and
the first input comprises a selection of one or more of the menu objects of the sixth subset representing contextual information of the patient.

15. The system of claim 1, wherein:
the first set of one or more menu objects comprises a seventh subset of menu objects, wherein each of the menu objects of the seventh subset represents a respective potential symptom quality; and the first input comprises a selection of one or more of the menu objects of the seventh subset representing a symptom quality of the patient.

16. The system of claim 1, wherein:
the first set of one or more menu objects comprises an eighth subset of menu objects, wherein each of the menu objects of the eighth subset represents a respective potential prior medical condition; and
the first input comprises a selection of one or more of the menu objects of the eighth subset representing a prior medical condition of the patient.

17. The system of claim 1, wherein:
the first set of one or more menu objects comprises a ninth subset of menu objects, wherein each of the menu objects of the ninth subset represents a respective potential current medication; and
the first input comprises a selection of one or more of the menu objects of the ninth subset representing a current medication of the patient.

18. The system of claim 1, wherein:
the first set of one or more menu objects comprises a tenth subset of menu objects, wherein each of the menu objects of the tenth subset represents a respective potential medication to be prescribed; and
the first input comprises a selection of one or more of the menu objects of the tenth subset representing a medication to be prescribed for the patient.

19. The system of claim 1, wherein:
the first set of one or more menu objects comprises an eleventh subset of menu objects, wherein each of the menu objects of the eleventh subset represents a respective potential treatment to be prescribed; and
the first input comprises a selection of one or more of the menu objects of the eleventh subset representing a treatment to be prescribed for the patient.

20. The system of claim 1, wherein:
the first set of one or more menu objects comprises a first field configured to accept entry of character strings;
the first input comprises entry of a first character string into the first field; and
generating the natural-language statement based on the medical information indicated by the first user input comprises inserting the character string into a predetermined natural-language sentence structure.

21. The system of claim 1, wherein:
the first set of one or more menu objects comprises a second field configured to accept entry of character strings;
the first input comprises entry of a second character string into the second field; and
generating the natural-language statement based on the medical information indicated by the first user input comprises inserting the character string into a predetermined natural-language paragraph structure as a complete sentence.

22. The system of claim 1, wherein the one or more processors are configured to cause the system to, in accordance with the first user input, dynamically update the menu region.

23. The system of claim 1, wherein the one or more processors are configured to cause the system to:
detect a fourth user input comprising an instruction to manually modify the natural-language statement displayed in the canvas region;
in response to detecting the fourth user input, update the displayed natural-language statement displayed in the canvas region.

24. The system of claim 1, wherein:
displaying the natural-language statement in the canvas region comprises displaying the natural-language statement using a first format; and
the one or more processors are configured to cause the system to display a review screen on which the natural-language statement is displayed using a second format.

25. The system of claim 1, wherein the one or more processors are configured to cause the system to capture and store metadata representing the first input.

26. The system of claim 1, wherein updating display of the canvas region to display the natural-language statement is performed automatically in response to detection of the first user input.

27. The system of claim 1, wherein the system is configured such that only one menu object of the first set of menu objects are able to be selected at once.

28. The system of claim 1, wherein the system is configured such that multiple menu objects of the first set of menu objects are able to be selected at once.

29. A non-transitory computer-readable storage medium storing instructions for generating a natural-language statement for a healthcare record, the instructions configured to be executed by a system comprising one or more processors to cause the system to:
display a graphical user interface comprising a canvas region and a menu region, wherein the menu region comprises a first set of one or more interactive graphical user interface menu objects configured to receive user inputs corresponding to medical information, wherein one or more of the menu objects is able to be toggled between two or more states selected from: positively indicated, negatively indicated, neither positively nor negatively indicated, and the menu objects in the menu region are displayed in accordance with a one or more templates selected by a user of the graphical user interface, the one or more templates controlling the menu objects that are displayed in the menu region and an order in which the menu objects are displayed in the menu region; and
receive data representing a first user input comprising user interaction with one or more of the first set of menu objects, the first input indicating medical information for a patient;
in accordance with the first user input:
generate a natural-language statement based on the medical information indicated by the first user input and in accordance with the one or more templates selected by the user of the graphical user interface; and
update display of the canvas region to display the natural-language statement.

30. A method for generating a natural-language statement for a healthcare record, the method performed at a system comprising one or more processor, the method comprising:
displaying a graphical user interface comprising a canvas region and a menu region, wherein the menu region comprises a first set of one or more interactive graphical user interface menu objects configured to receive user inputs corresponding to medical information, wherein one or more of the menu objects is able to be toggled between two or more states selected from: positively indicated, negatively indicated, neither positively nor negatively indicated, and the menu objects in the menu region are displayed in accordance with one or more templates selected by a user of the graphical user interface, the one or more templates controlling the menu objects that are displayed in the menu region and an order in which the menu objects are displayed in the menu region; and receiving data representing a first user input comprising user interaction with one or more of the first set of menu objects, the first input indicating medical information for a patient;

in accordance with the first user input:
generating a natural-language statement based on the medical information indicated by the first user input and in accordance with the one or more templates selected by the user of the graphical user interface; and updating display of the canvas region to display the natural-language statement.

31. The system of claim 1, wherein the one or more templates are selected from a template library comprising a plurality of templates based on patient complaint type, medical setting, and/or use case.

* * * * *